United States Patent
Adachi et al.

(10) Patent No.: US 11,444,248 B2
(45) Date of Patent: *Sep. 13, 2022

(54) ORGANIC ELECTRO-LUMINESCENT ELEMENT AND BIOINSTRUMENTATION DEVICE

(71) Applicants: Kyushu University, National University Corporation, Fukuoka (JP); HAMAMATSU PHOTONICS K.K., Hamamatsu (JP)

(72) Inventors: Chihaya Adachi, Fukuoka (JP); Hajime Nakanotani, Fukuoka (JP); Takahiko Yamanaka, Hamamatsu (JP); Shigeo Hara, Hamamatsu (JP); Toru Hirohata, Hamamatsu (JP)

(*) Notice: Subject to any disclaimer, the term of this patent is extended or adjusted under 35 U.S.C. 154(b) by 672 days.

This patent is subject to a terminal disclaimer.

(21) Appl. No.: 15/823,601

(22) Filed: Nov. 28, 2017

(65) Prior Publication Data

US 2018/0151810 A1 May 31, 2018

(30) Foreign Application Priority Data

Nov. 30, 2016 (JP) .............................. JP2016-233256
Sep. 22, 2017 (JP) .............................. JP2017-182853

(51) Int. Cl.
*H01L 51/00* (2006.01)
*G01N 21/64* (2006.01)
(Continued)

(52) U.S. Cl.
CPC .......... *H01L 51/0072* (2013.01); *C09K 11/06* (2013.01); *G01N 21/6486* (2013.01);
(Continued)

(58) Field of Classification Search
CPC ............ H01L 51/0062; H01L 51/0071; H01L 51/0072; H01L 51/5024; H01L 51/5028; C07D 279/18; C07D 219/04
See application file for complete search history.

(56) References Cited

U.S. PATENT DOCUMENTS 8,279,443 B2 * 10/2012 Ueda .................... A61B 5/0091
356/432
10,228,328 B2 * 3/2019 Adachi ............... H01L 51/5004
(Continued)

FOREIGN PATENT DOCUMENTS

CN       104830320      8/2015
JP       2012-219078    11/2012
(Continued)

OTHER PUBLICATIONS

Wang, Shipan et al. "Highly Efficient Near-Infrared Delayed Fluorescence Organic Light Emitting Diodes Using a Phenanthrene-Based Charge-Transfer Compound." 2015. Angew. Chem. Int. Ed. 54: 13068-13072 (Year: 2015).*
(Continued)

*Primary Examiner* — Marla D McConnell
*Assistant Examiner* — Jenna N Chandhok
(74) *Attorney, Agent, or Firm* — Soei Patent & Law Firm

(57) ABSTRACT

An organic electro-luminescent element having a luminescence peak in a near-infrared range, comprising a positive electrode, a negative electrode, and at least one organic layer including a luminescent layer located between the positive electrode and the negative electrode, wherein the luminescent layer comprises a host material, a delayed fluorescent material and a luminescent material, wherein each of the delayed fluorescent material and the luminescent material have a structure with two or three benzene rings bonded to an N atom.

10 Claims, 5 Drawing Sheets

(51) Int. Cl.
| | |
|---|---|
| C09K 11/06 | (2006.01) |
| C07D 279/18 | (2006.01) |
| C07D 209/82 | (2006.01) |
| C07D 219/04 | (2006.01) |
| C07D 265/38 | (2006.01) |
| A61B 5/00 | (2006.01) |
| H01L 51/50 | (2006.01) |

(52) U.S. Cl.
CPC ........ *H01L 51/0059* (2013.01); *A61B 5/0059* (2013.01); *C07D 209/82* (2013.01); *C07D 219/04* (2013.01); *C07D 265/38* (2013.01); *C07D 279/18* (2013.01); *H01L 51/5024* (2013.01)

(56) References Cited

U.S. PATENT DOCUMENTS

| | | | |
|---|---|---|---|
| 2013/0037785 A1 | 2/2013 | Fujita et al. | |
| 2016/0164020 A1* | 6/2016 | Kim | H01L 51/5028 257/40 |
| 2016/0190478 A1 | 6/2016 | Nakanotani et al. | |
| 2016/0359117 A1* | 12/2016 | Hamade | H01L 51/0061 |
| 2016/0372688 A1 | 12/2016 | Seo et al. | |
| 2017/0123268 A1 | 5/2017 | Sasaki et al. | |
| 2017/0324055 A1 | 11/2017 | Ishisone et al. | |
| 2018/0149595 A1 | 5/2018 | Adachi et al. | |
| 2019/0214578 A1* | 7/2019 | Sugawara | C09K 11/06 |

FOREIGN PATENT DOCUMENTS

| | | |
|---|---|---|
| JP | 2012-221082 | 11/2012 |
| JP | 2013-038245 | 2/2013 |
| JP | 2014-082405 | 5/2014 |
| JP | 5669163 | 12/2014 |
| JP | 2015-038859 | 2/2015 |
| JP | 2015-143916 | 8/2015 |
| JP | 2015-228460 | 12/2015 |
| JP | 2016-119355 | 6/2016 |
| JP | 2018-092993 | 6/2018 |
| WO | 2016/017757 | 2/2016 |
| WO | 2016/181773 | 11/2016 |
| WO | 2016/181844 | 11/2016 |

OTHER PUBLICATIONS

G. Qian et al., "Synthesis and Application of Thiadiazoloquinoxaline-Containing Chromophores as Dopants for Efficient Near-Infrared Organic Light-Emitting Diodes", J. Phys. Chem. C, 2009, P1589-P1595, vol. 113.

X. Du et al., "Efficient Non-doped Near Infrared Organic Light-Emitting Devices Based on Fluorophores with Aggregation-Induced Emission Enhancement", Chemistry of Materials, 2012, P2178-P2185, vol. 24.

G. Qian et al., "Simple and Efficient Near-Infrared Organic Chromophores for Light-Emitting Diodes with Single Electroluminescent Emission above 1000nm", Advanced Materials, 2009, P111-P116, vol. 21.

J. Mayerhoffer et al., "Synthesis and Molecular Properties of Acceptor-Substituted Squaraine Dyes", Chemistry a European Journal, 2013, P218-P232, vol. 19.

M. T. Sharbati et al., "Near-infrared electroluminescence from organic light emitting diode based on Imine oligomer with low turn on voltage", Optik, 2013, P52-P54, vol. 124.

X. Zhang et al., "Long-Wavelength, Photostable, Two-Photon Excitable BODIPY Fluorophores Readily Modifiable for Molecular Probes", The Journal of Organic Chemistry, 2013, P9153-P9160, vol. 78.

S. Wang et al., "Highly Efficient Near-Infrared Delayed Fluorescence Organic Light Emitting Diodes Using a Phenanthrene-Based Charge-Transfer Compound", Angewandte Chemie International Edition, 2015, P1-P6 vol. 54.

J. Lee et al., "Controlled emission colors and singlet-triplet energy gaps of dihydrophenazine-based thermally activated delayed fluorescence emitters", Journal of Materials Chemistry C, 2015, P2175-P2181, vol. 3.

Q. Zhang et al., "Anthraquinone-Based Intramolecular Charge-Transfer Compounds: Computational Molecular Design, Thermally Activated Delayed Fluorescence, and Highly Efficient Red Electroluminescence", Journal of the American Chemical Society, 2014, P18070-P18081, vol. 136.

H. Uoyama et al., "Highly efficient organic light-emitting diodes from delayed fluorescence", Nature, Dec. 13, 2012, P234-P238, vol. 492.

SOEI Statement of Related Matters identifying the U.S. Patent Publication No. US2018/0149595A1, Jul. 27, 2018, 1 page.

Nakanotani, H. et al. High-efficiency organic light-emitting diodes with fluorescent emitters. Nat. Commun. 5: 4016 (2014), Macmillan Publishers Limited.

H. Nakanotani et al., "High Performance Organic Light-emitting Diodes Based on Thermally-activated Delayed Fluorescence Materials", Journal of the Vacuum Society of Japan vol. 58, No. 3, 2015, P73-P78.

Office Action issued in Japanese Patent Application No. P2017-182853, dated Feb. 16, 2021 (with English machine translation).

* cited by examiner

ORGANIC ELECTRO-LUMINESCENT ELEMENT AND BIOINSTRUMENTATION DEVICE

CROSS-REFERENCE TO RELATED APPLICATIONS

This application claims the benefit of priority from Japanese Patent Applications No. 2016-233256, filed on Nov. 30, 2016 and No. 2017-182853, filed on Sep. 22, 2017, the entire contents of which are incorporated herein by reference. Additionally, this application includes related subject matter to U.S. Patent Application entitled "Organic Electro-Luminescent Element and Bioinstrumentation Device", filed on Nov. 28, 2017, which claims the benefit of priority from Japanese Patent Application No. 2016-233234, filed on Nov. 30, 2016, the entire contents of which are incorporated herein by reference.

FIELD

An organic electro-luminescent element and bioinstrumentation device using the same.

BACKGROUND

Organisms contain a large number of substances, having absorption in every wavelength range. The near-infrared range is hard to be absorbed by organisms compared to other wavelength ranges, so that biological sensing can be achieved by using the light in the near-infrared range. Specifically, biological sensing can be performed by a bioinstrumentation device including a near-infrared luminescent element and a photo detector, which is brought into close contact with an organic material, such as skin, for irradiating an organism with light, the detector detecting scattered light from the inside of the organism.

Solid-state elements based on inorganic semiconductors have been used as conventional luminescent elements. Although devices using solid-state elements have been widely used in the field of bioinstrumentation, solid-state elements have problems such as poor biocompatibility in a broad sense including design freedom and flexibility.

In contrast, organic electro-luminescent elements (hereinafter also referred to as "organic EL elements"), which recently have attracted attention, may be used as luminescent elements to solve the problem. In other words, organic EL elements are excellent in processability and design freedom due to material properties and manufacturing process, and furthermore, flexibility may also be imparted to organic EL elements by deposition on a plastic substrate. Organic EL elements that emit light in a near-infrared range, such as those described in Non Patent Literature 1 to 6 are known.

CITATION LIST

[Patent Literature 1] JP5669163 B1
[Non Patent Literature 1] G. Qian et al. J. Phys. Chem. C 2009, 113, 1589-1595
[Non Patent Literature 2] X. Du et al. Chem. Mater. 2012, 24, 2178-2185
[Non Patent Literature 3] G. Qian et al. Adv. Mater. 2009, 21, 111-116
[Non Patent Literature 4] U. Mayerhoeffer et al. Chem. Eur. J. 2013, 19, 218-232
[Non Patent Literature 5] M. T. Sharbatia et al. Optik, 2013, 124, 52-54
[Non Patent Literature 6] X. Zhang et al. J. Org. Chem. 2013, 78, 9153-9160

SUMMARY

The organic EL elements described in Non Patent Literature 1 to 6, however, have room for improvement in the luminous efficiency thereof. Patent Literature 1 discloses that an organic EL element having a high luminous efficiency can be provided by using a delayed fluorescent material as assistant dopant. The present inventors have found it difficult to manufacture organic EL elements that emit light in the near-infrared range applicable for use in bioinstrumentation based on the disclosure of Patent Literature 1.

An object of the present invention is, therefore, to provide an organic EL element that emits light in a near-infrared range, with a high luminous efficiency, and a bioinstrumentation device using the same. The near-infrared range may generally be understood to include a lower limit of approximately 700 nm and an upper limit of approximately 2500 nm. By way of non-exhaustive examples, some embodiments of the present invention may be configured to operate in a near-infrared range of approximately 700 nm to 800 nm, or near the maximum luminescence values. In still other example embodiments, the upper limit of the near-infrared range may be approximately 900 nm or approximately 1000 nm according to different example configurations.

The present invention includes an organic EL element having a luminescence peak in a near-infrared range, comprising a positive electrode, a negative electrode, and at least one organic layer including a luminescent layer located between the positive electrode and the negative electrode. The luminescent layer comprises a host material, a delayed fluorescent material and a luminescent material. Each of the delayed fluorescent material and the luminescent material may have an N-containing structure with two or three benzene rings bonded to an N atom, wherein two of the benzene rings are optionally bonded to each other to form a fused ring.

The N-containing structure may be a structure selected from formulas (1) to (6). In some example embodiments, the structure of the delayed fluorescent material selected from formulas (1) to (6) may also be selected as the N-containing structure of the luminescent material, i.e. the structure of the delayed fluorescent material selected from formulas (1) to (6) may be the same as the structure of the luminescent material selected from formulas (1) to (6). For example, when the delayed fluorescent material has a structure represented by formula (1), the luminescent material may also have a structure represented by formula (1).

[Chemical Formula 1]

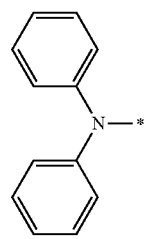

(1)

(2) 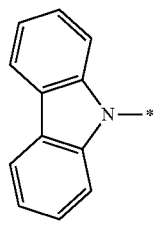

(3) 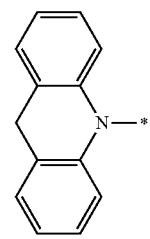

(4) 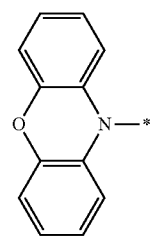

(5) 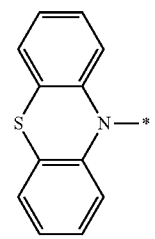

(6) 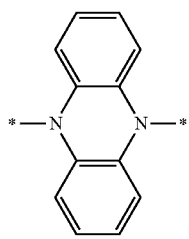

In still other example embodiments, the N-containing structure may be a structure represented by formula (7).

[Chemical Formula 2]

(7) 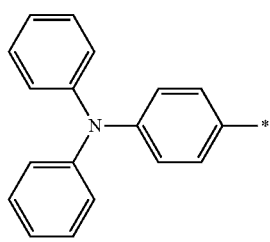

In some embodiments, the N-containing structure represented by formula (1) to (7) may have one or more substituents. The examples of the substituents include alkyl groups having 1 to 6 carbon atoms, aryl groups having 6 to 10 carbon atoms and cyano groups.

Additionally, both of the delayed fluorescent material and the luminescent material further may have a fused ring structure in addition to the N-containing structure. In some example embodiments, the fused ring structure of the delayed fluorescent material and the luminescent material each comprise an equivalent set of at least two successive rings, i.e. the fused rings of the delayed fluorescent material and the luminescent material have a common structure of at least two successive rings.

Although the reason why the organic EL element of the present invention has a high luminous efficiency due to having at least any of the constituent features described above is not clearly understood, the present inventors presume the reason as follows. A near-infrared luminescent material is required to extend the w-conjugated length of electron orbit as a basic design principle. Many functional substituents such as a group having a specific amino group, an aromatic fused ring, and an aromatic heterocycle are therefore required to be introduced into a molecule. On the other hand, it is presumed that a molecule having many functional substituents tends to suppress the interaction between different molecules due to the polarity of molecule and steric effects. Particularly in a luminescence phenomenon based on Forster energy transfer, the distance and orientation factor between host and guest molecules is an important driving force, so that the interaction between the host and guest molecules is very important. When each of the host and guest materials in energy transfer has a common unit, the interaction between the molecules is enhanced due to chemical analogy, so that improvement in energy transfer efficiency is expected. It is presumed that a high energy transfer efficiency is achieved in an organic EL element having a luminescence peak in a near-infrared range by introduction of a common unit to both of the delayed fluorescent material and the luminescent material.

Additionally, some of the example embodiments include a bioinstrumentation device comprising the organic EL element and a photo detector.

An organic EL element that emits light in a near-infrared range, with a high luminous efficiency can be provided with a bioinstrumentation device.

DETAILED DESCRIPTION

Hereinafter, the present invention will be described in detail. Although the following constituent features will be described based on typical embodiments or specific examples of the present invention in some cases, the present invention is not limited to such embodiments or specific examples. A numerical range represented using "to" herein means a range containing the numerical values provided before and after the word "to" as the lower limit value and the upper limit value, respectively. The isotope species of hydrogen atoms present in the compound molecule for use in the present invention are not particularly limited. For example, all of the hydrogen atoms in the molecule may be $^1$H, or all or a part of the hydrogen atoms thereof may be $^2$H (deuterium D).

Herein, "host material" means an organic compound that confines at least the energy of a delayed fluorescent material in a luminescent layer; "delayed fluorescent material" means an organic compound that is capable of being transferred to the triplet excited state and then undergoing inverse intersystem crossing to the singlet excited state, and emits fluorescent light on returning from the singlet excited state to the ground state; and "luminescent material" means an organic compound that allows substantially no inverse intersystem crossing different from a delayed fluorescent material, but emits fluorescence when returned from the excited singlet state to the ground state.

[Layer Structure of Organic EL Element]

The organic EL element of the present invention comprises a positive electrode, a negative electrode, and at least one organic layer including a luminescent layer located between the positive electrode and the negative electrode.

Figure 1:
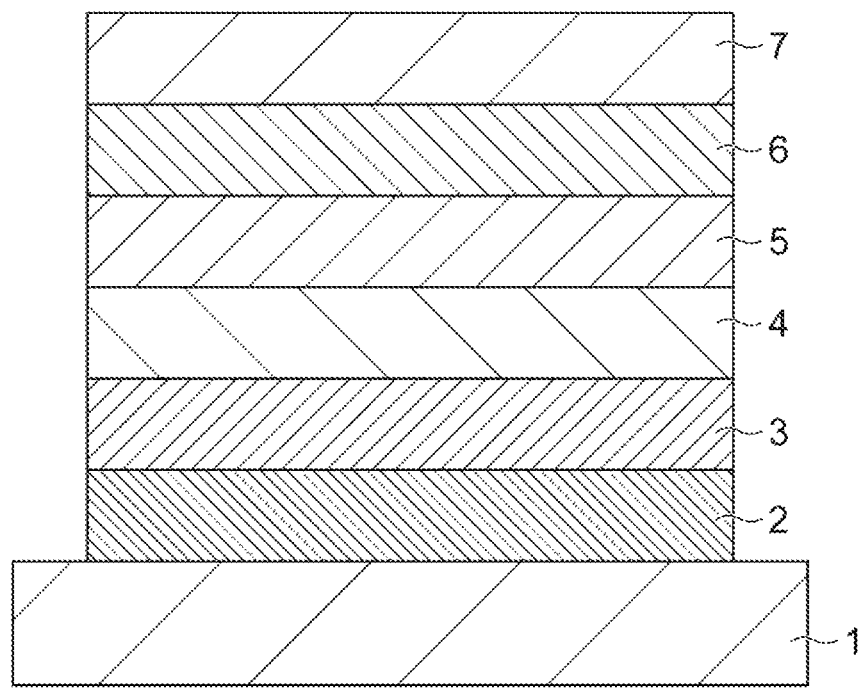
FIG. 1 is a schematic cross-sectional view showing a layer structure of an organic EL element.

The organic layer may consist of a luminescent layer only, or may include one or more organic layers in addition to the luminescent layer. Examples of such other organic layers include a hole transport layer, a hole injection layer, an electron blocking layer, a hole blocking layer, an electron injection layer, an electron transport layer, and an exciton blocking layer. The hole transport layer may be a hole injection/transport layer having a hole injection function, and the electron transport layer may be an electron injection/transport layer having an electron injection function. An example structure of a specific organic EL element is shown in FIG. 1. In FIG. 1, a substrate 1, a positive electrode 2, a hole injection layer 3, a hole transport layer 4, a luminescent layer 5, an electron transport layer 6, and a negative electrode 7 are shown.

Hereinafter, each of the components and each of the layers of an organic EL element-will be described.

[Luminescent Layer]

The luminescent layer is a layer where holes and electrons injected from the anode and the cathode respectively are recombined to form excitons, and then the layer emits light. In some example embodiments of the organic EL element, the luminescent layer comprises a host material, a delayed fluorescent material and a luminescent material. Each of the delayed fluorescent material and the luminescent material may have a N-containing structure with two or three benzene rings bonded to an N atom, wherein two of the benzene rings are optionally bonded to each other to form a fused ring.

In the N-containing structure with two or three benzene rings bonded to an N atom, the two benzene rings may be bonded through, for example, a single bond, a carbon atom, an oxygen atom, a sulfur atom, or a nitrogen atom so as to form a fused ring. In the case of bonding through a carbon atom, the carbon atom may have one or two substituents, or may form a carbonyl group together with an oxygen atom. Specific examples of the fused ring that can be formed include the structures represented by formulas (2) to (6).

In some example embodiments, it is preferable that the structure described above be a structure represented by formula (1) or (2). In other example embodiments, it is more preferable that the structure be a structure represented by formula (1). And in still example embodiments, it is more preferable that the structure be a structure represented by formula (7).

Although the benzene ring may further form a fused ring such as a naphthalene ring together with another aromatic ring or heterocycle, in some example embodiments it is preferable that the benzene ring not form a fused ring.

In some example embodiments, it is preferable that each of the delayed fluorescent material and the luminescent material further have a fused ring in addition to the N-containing structure described above, and the fused ring structure of the delayed fluorescent material and the luminescent material each comprise an equivalent set of at least two successive rings, i.e. the fused rings of the delayed fluorescent material and the luminescent material having a common structure of at least two successive rings. Examples of such structures include the structures shown below.

[Chemical Formula 3]

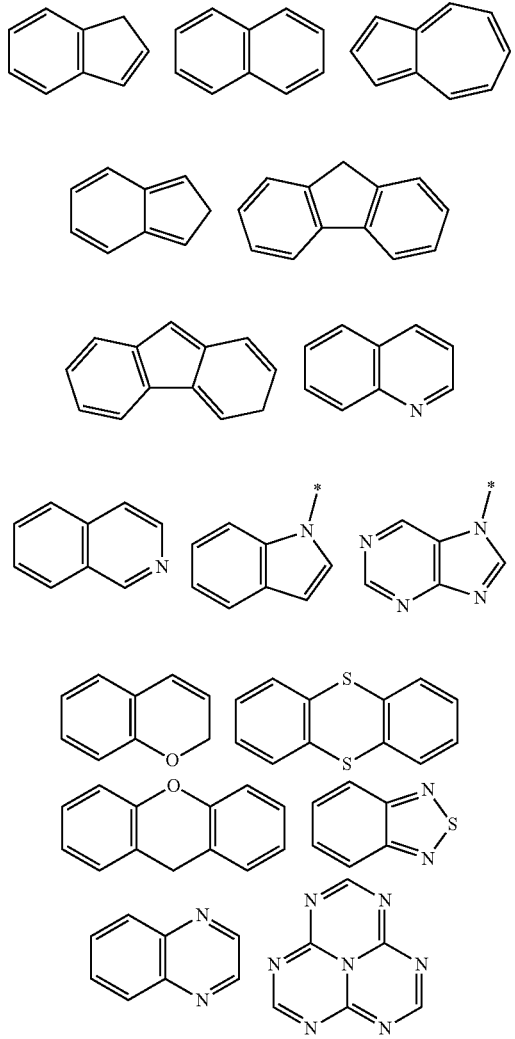

Regarding the structures in the fused rings, the apparent position of the double bonds in the chemical formulas are not necessarily the same because the double bonds are delocalized in the fused rings. For example, when comparing the two successive rings encircled by the broken lines in the following formulas (A) and (B), the position of the double bonds is different; however, the two successive rings in the formula (A) are equivalent to those in the formula (B). Specifically, the fused ring represented by formula (B) can also be represented by the following formula (B').

[Chemical Formula 4]

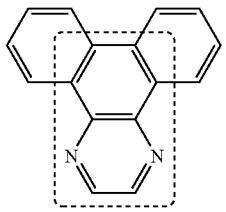
(A)

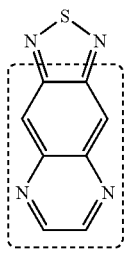
(B)

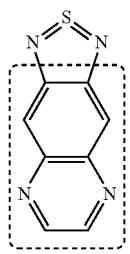
(B')

In some example embodiments, it is also preferable that each of the delayed fluorescent material and the luminescent material further has a common heterocycle (preferably an aromatic heterocycle) or a cyano group, in addition to the N-containing structures described above. Examples of the heterocycles include the structures shown below. These heterocycles may further form a fused ring together with another benzene ring or heterocycle.

[Chemical Formula 5]

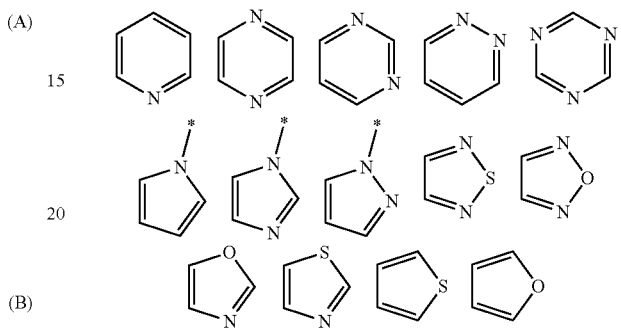

(Host Material)

The host material is an organic compound that confines at least the energy of a delayed fluorescent material in a luminescent layer, and may further have at least a function for transporting carriers (electrons and/or holes) in the luminescent layer. In some example embodiments, it is preferable that the host material have a larger minimum excited triplet energy at 77 K than the delayed fluorescent material. The host materials may be used singly or in combinations of two or more thereof.

In some example embodiments, it is preferable that the host material be an organic compound that has a hole transport capability and an electron transport capability, prevents wavelength elongation of the emitted light, and also has a high glass transition temperature. Examples of preferred compounds which can be used as host material are shown below. In the structural formulas of the following example compounds, R and $R_1$ to $R_{10}$ each independently represent a hydrogen atom or a substituent; and n represents an integer of 3 to 5.

[Chemical Formula 6]

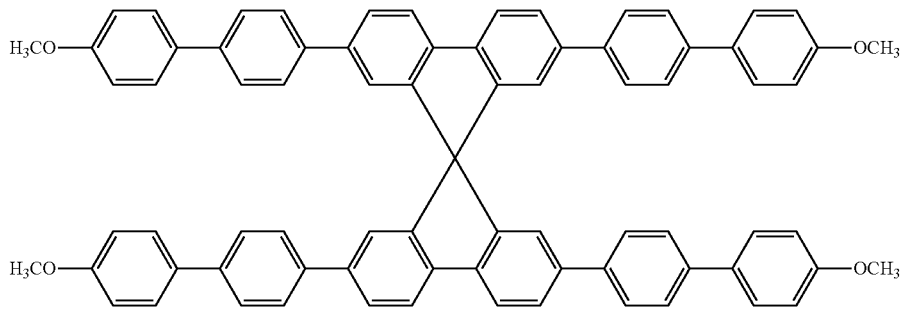

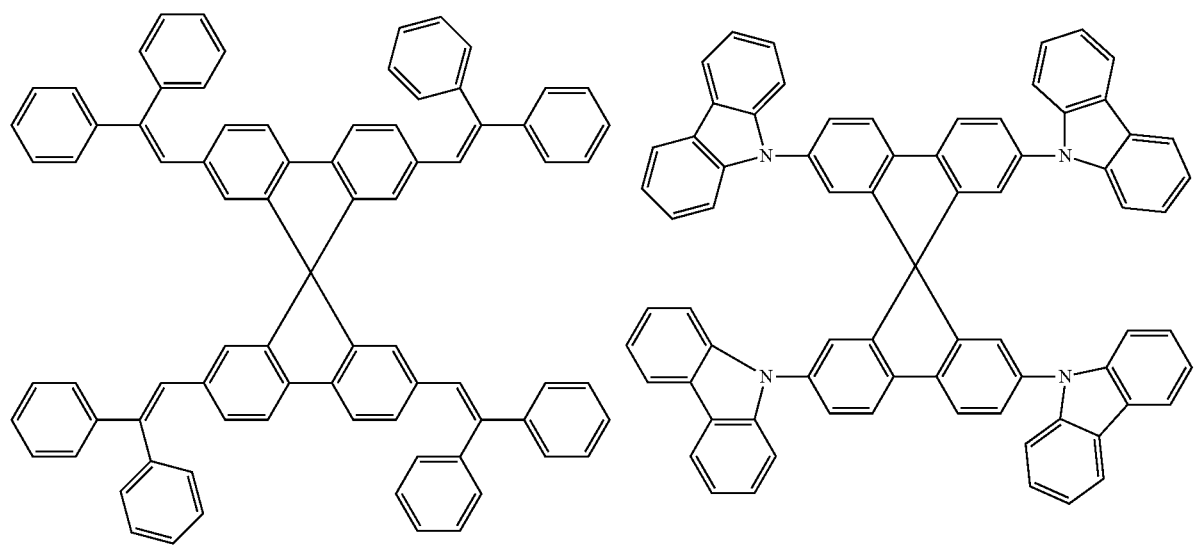
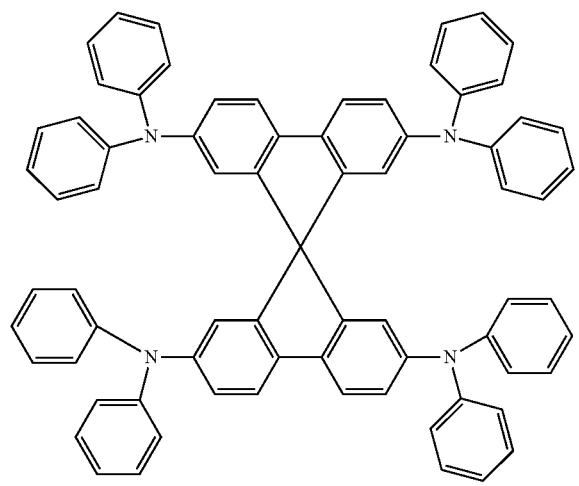
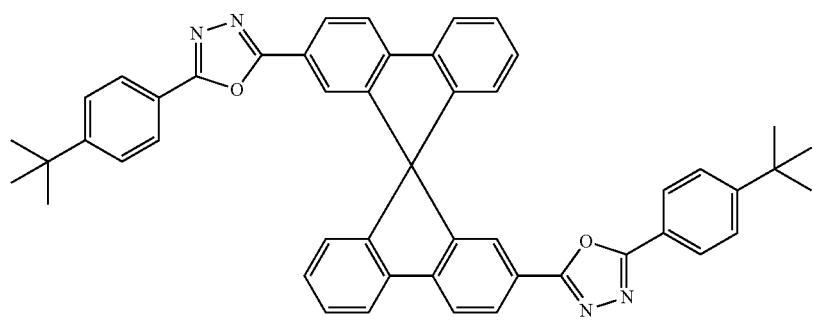

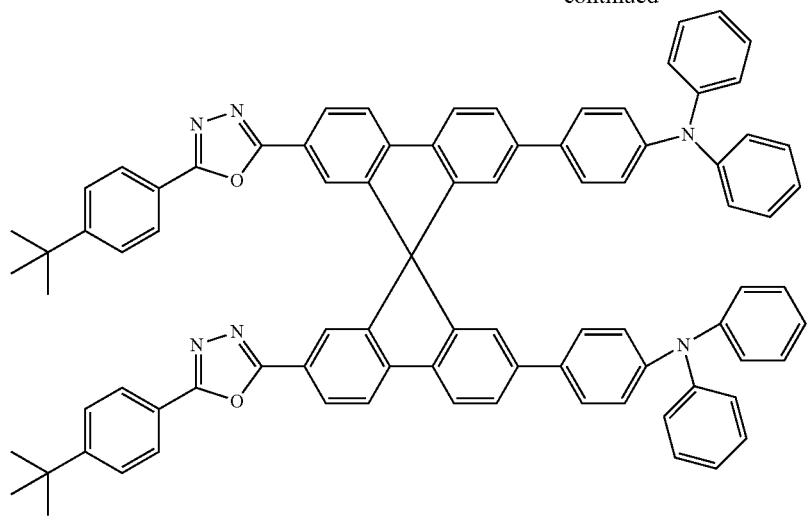
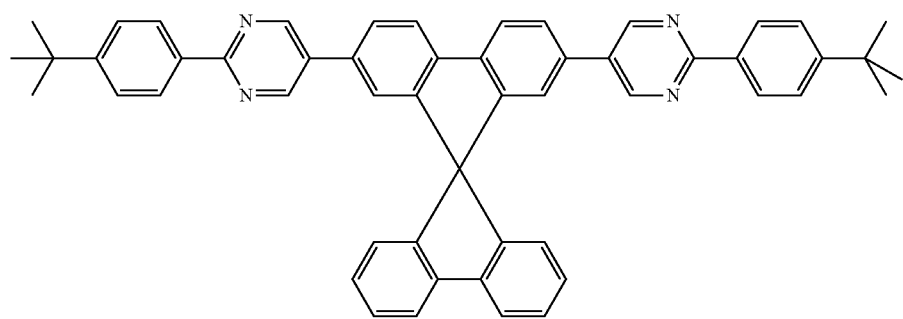
[Chemical Formula 7]
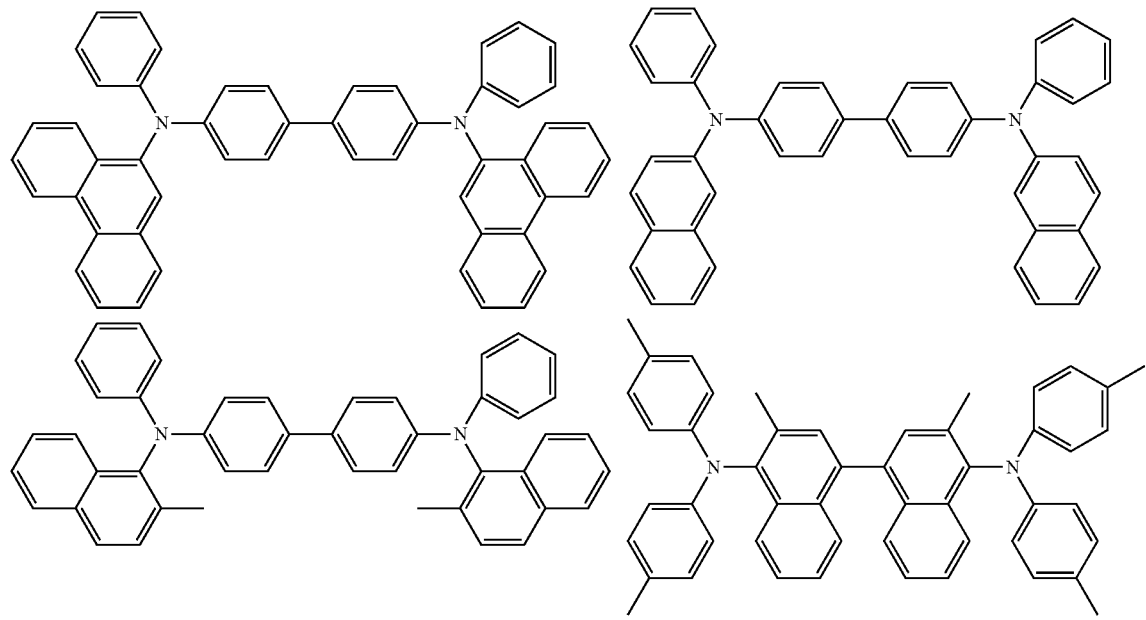

-continued
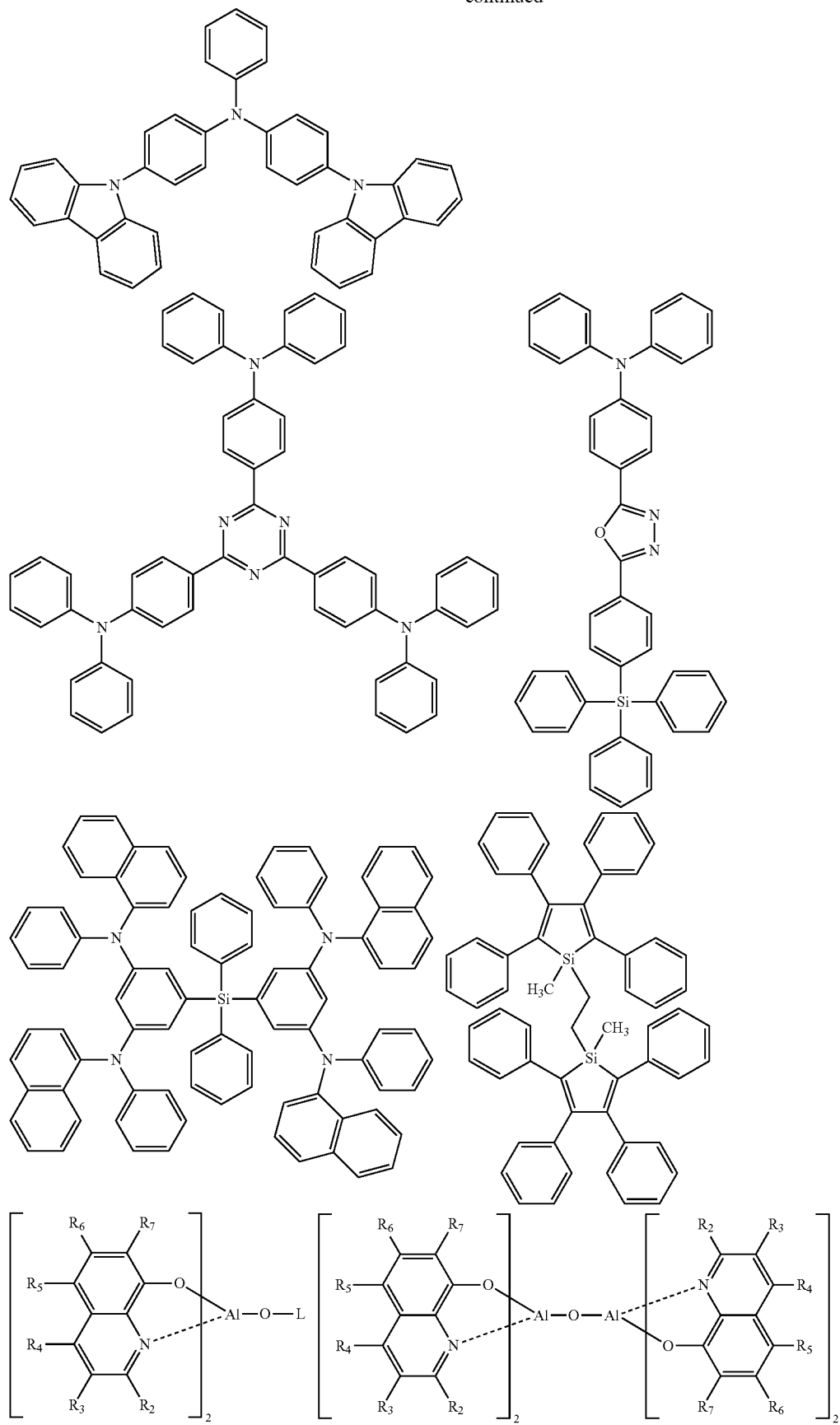

-continued
[Chemical Formula 8]
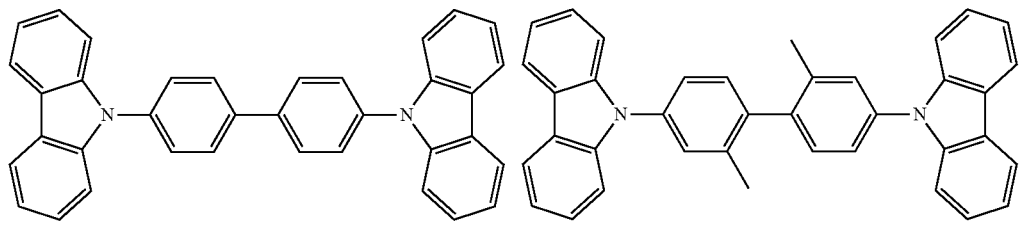
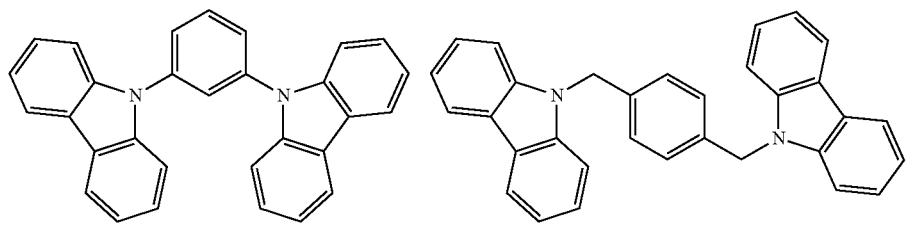
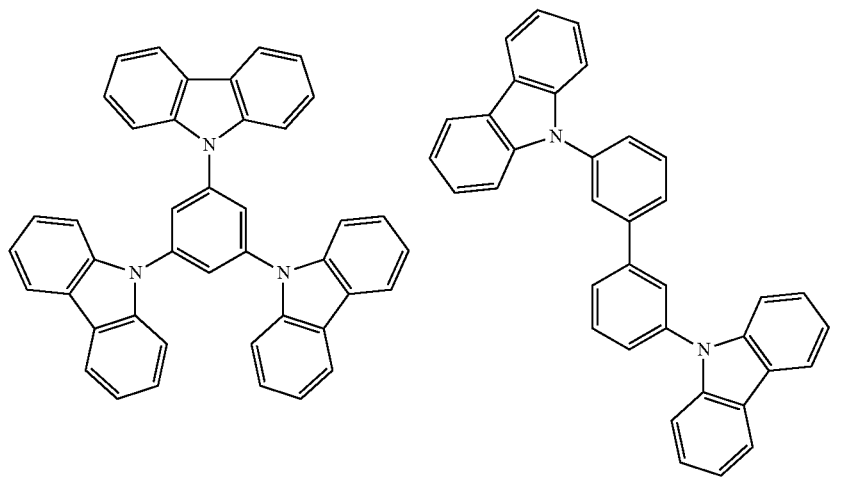
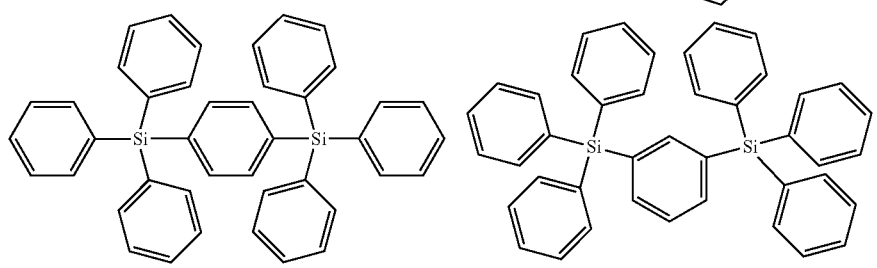
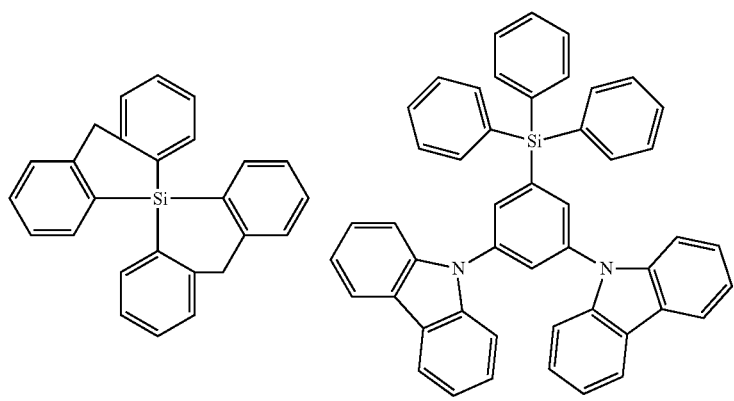

-continued
[Chemical Formula 9]
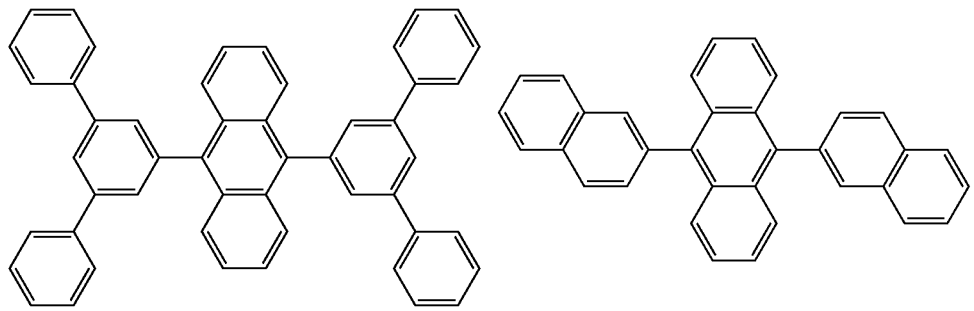
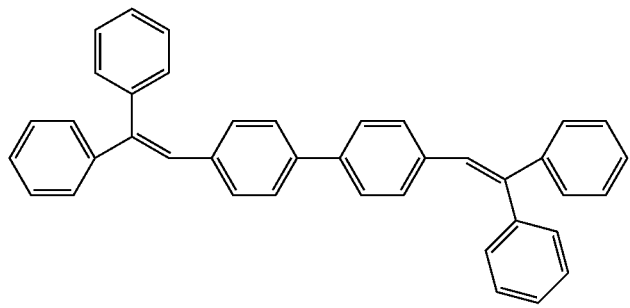
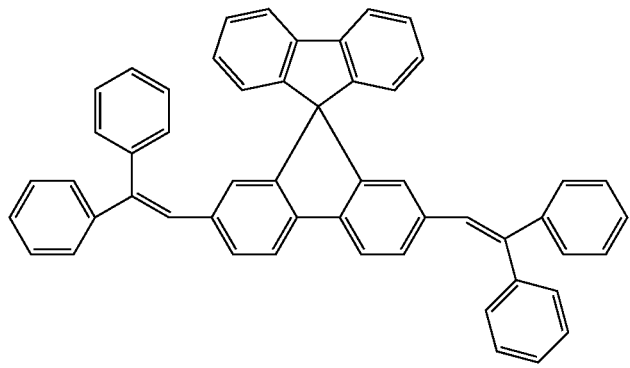
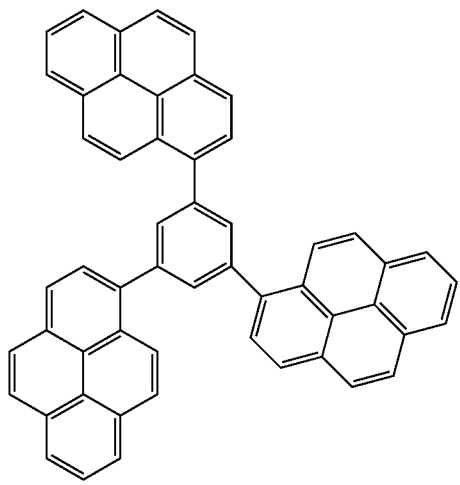

-continued
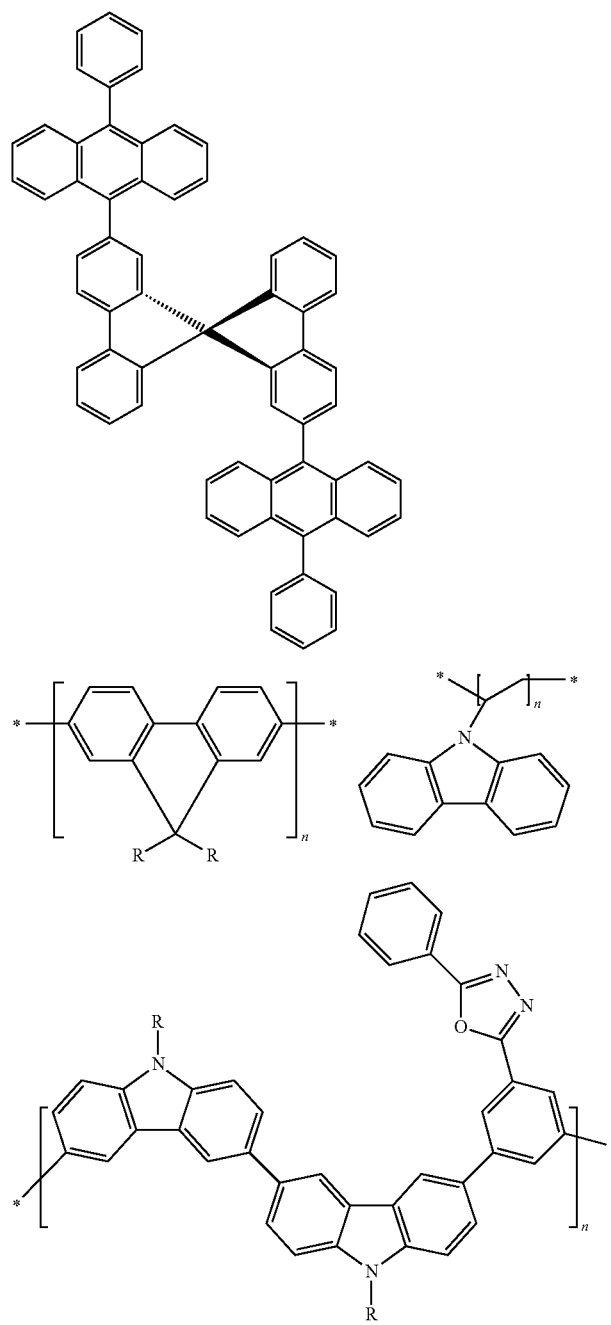
[Chemical Formula 10]
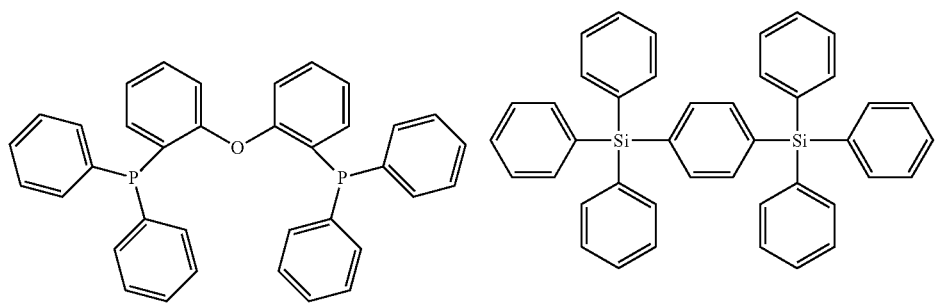

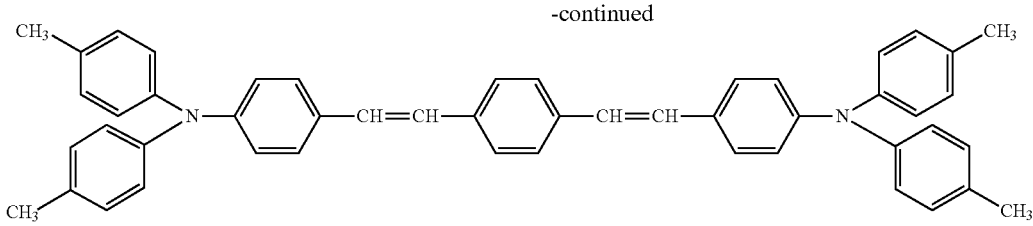

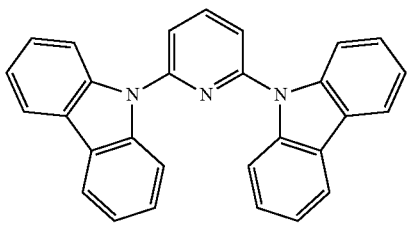

(Delayed Fluorescent Material)

In some example embodiments, it is preferable that the delayed fluorescent material be a thermally activated delayed fluorescent material that allows reverse intersystem crossing from an excited triplet state to an excited singlet state by absorption of thermal energy. The thermally activated delayed fluorescent material relatively easily allows reverse intersystem crossing from an excited triplet state to an excited singlet state by absorbing heat generated by a device and thus allows the excited triplet energy to efficiently contribute to light emission. In some example embodiments, it is preferable that the delayed fluorescent material be an organic compound that has a smaller minimum excited singlet energy than the host material and has a larger minimum excited singlet energy than the luminescent material.

The delayed fluorescent material has a difference $\Delta E_{st}$ between the energy level $E_{s1}$ in the minimum excited singlet state and the energy level $E_{T1}$ in the minimum excited triplet state at 77 K of 0.3 eV or less, 0.2 eV or less, 0.1 eV or less, and 0.08 eV or less. In some example embodiments, a lower difference $\Delta E_{st}$ may be preferable. With an energy difference $\Delta E_{st}$ in the range of approximately 0.3 eV or less, the delayed fluorescent material relatively easily allows reverse intersystem crossing from an excited triplet state to an excited singlet state, allowing the excited triplet energy to efficiently contribute to light emission.

In some example embodiments, it is preferable that a delayed fluorescent material that emits light in a normal red to deep red to near-infrared range when used as dopant be selected as the delayed fluorescent material. Specific examples thereof include the compounds shown below.

[Chemical Formula 11]

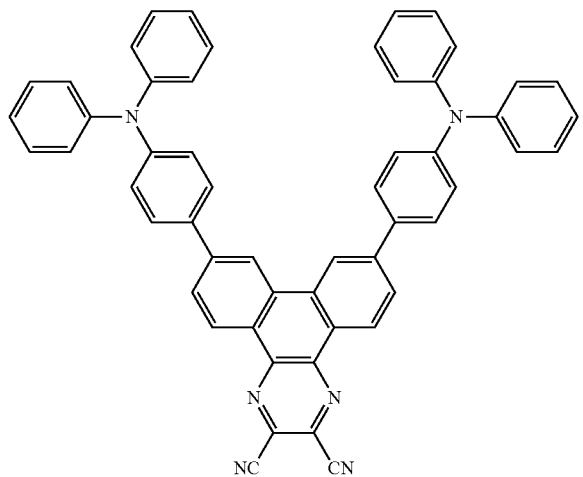

[Chemical Formula 12]

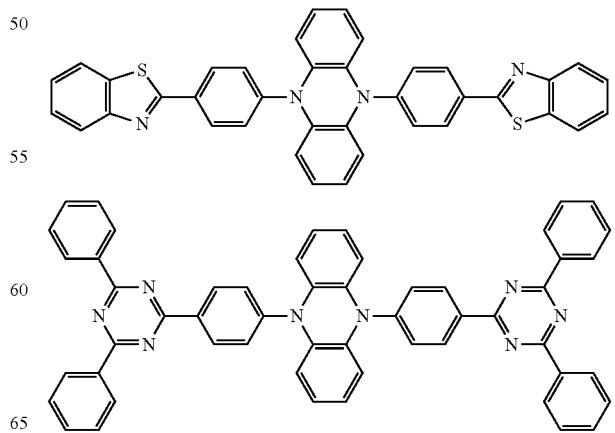

-continued

[Chemical Formula 13]

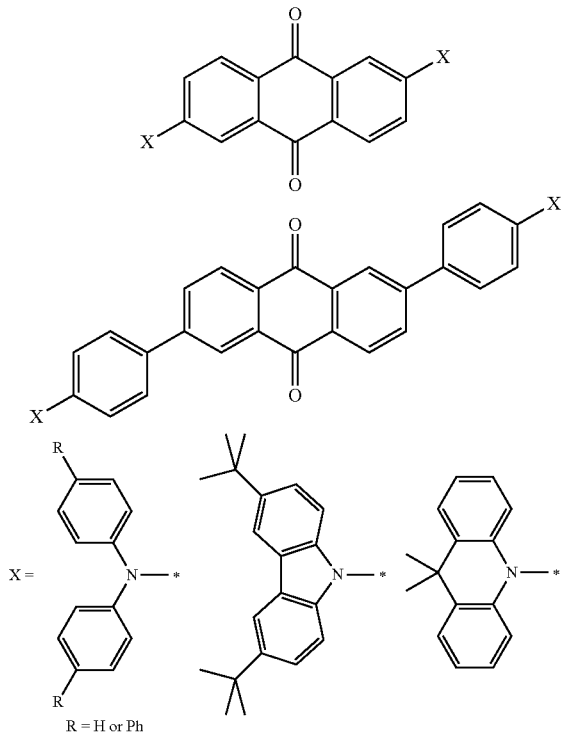

R = H or Ph

[Chemical Formula 14]

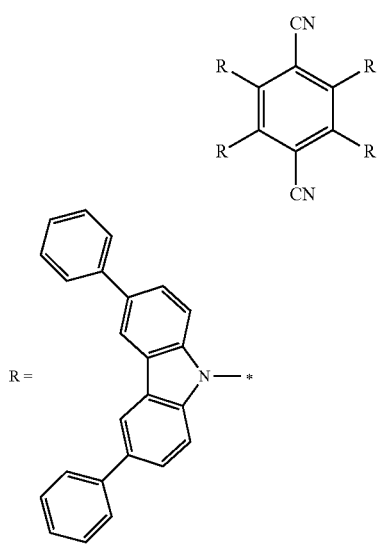

These compounds may be produced, for example, by the methods described in the following literatures.
S. Wang et al. Angew. Chem. Int. ed. 2015, 54, 1-6
J. Lee et al. J. Mater. Chem. C, 2015, 3, 2175-2181
Q. Zhang et al. J. Am. Chem. Soc. 2014, 136, 18070-18081
H. Uoyama et al. Nature 2012, 492, 234-238

(Luminescent Material)

The luminescent material receives energy from the host material in the excited singlet state and the delayed fluorescent material. The delayed fluorescent material in the excited singlet state reached from the excited triplet state through reverse intersystem crossing so as to transition to the singlet excited state, emits fluorescence when returned to the ground state. The luminescent material is not particularly limited as long as it can receive energy from the host material and the delayed fluorescent material so as to emit light, and the emitted light may be fluorescence or delayed fluorescence.

In some example embodiments, it is preferable that a luminescent material having a luminescence peak in a normal near-infrared range when used as dopant be selected as the luminescent material. Specific examples thereof include the compounds shown below.

[Chemical Formula 15]

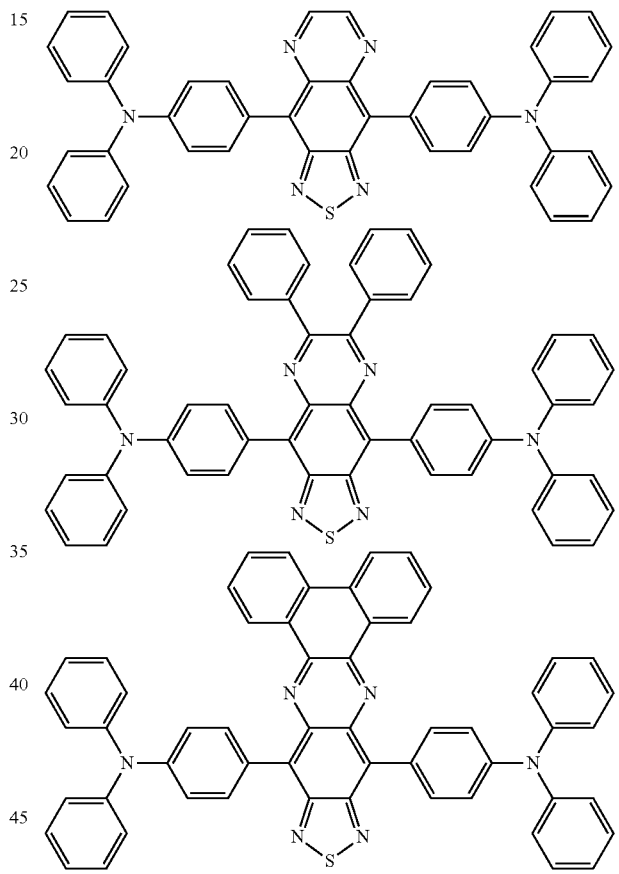

[Chemical Formula 16]

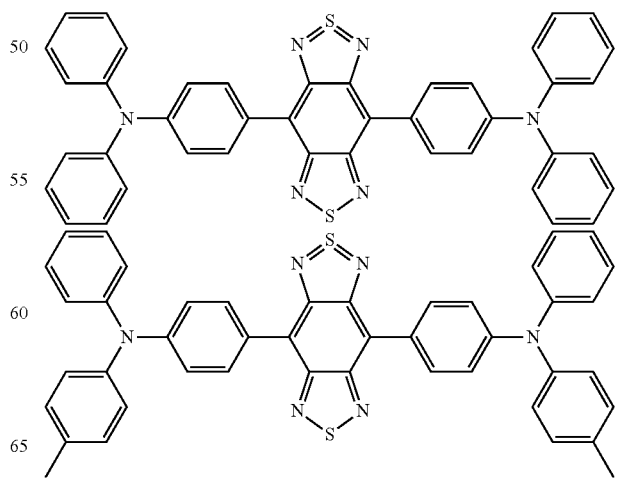

-continued

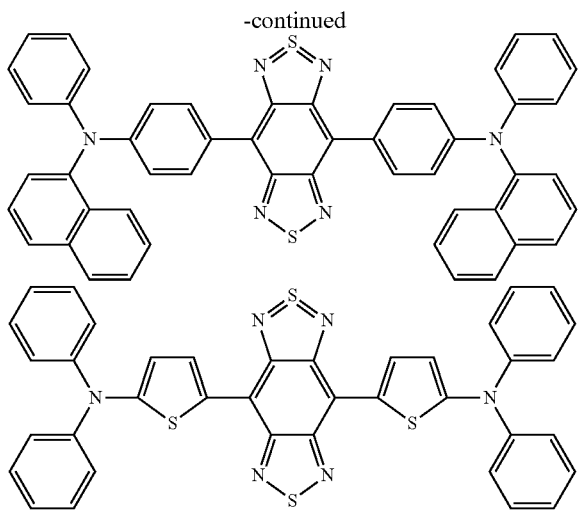

[Chemical Formula 17]

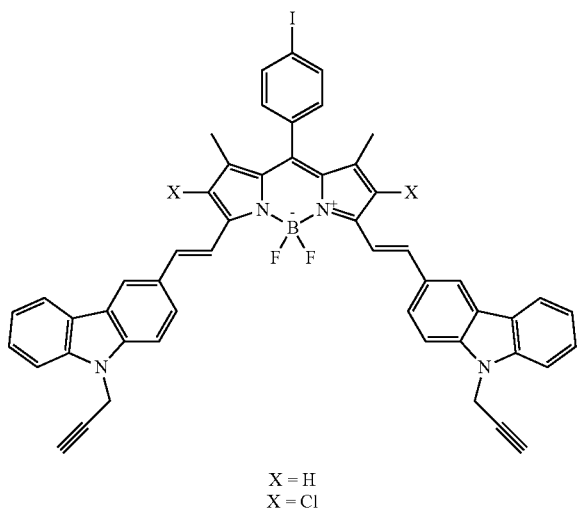

X = H
X = Cl

These compounds may be produced by, for example, the methods described in the following literatures.

G. Qian et al. J. Phys. Chem. C 2009, 113, 1589-1595
G. Qian et al. Adv. Mater. 2009, 21, 111-116
X. Zhang et al. J. Org. Chem. 2013, 78, 9153-9160

(Content of Host Material, Delayed Fluorescent Material and Luminescent Material)

Although the content of each organic compound contained in the luminescent layer is not particularly limited, it is preferable that the weight percentage of the delayed fluorescent material and the luminescent material each be smaller than the content of the host material. As a result, a higher luminous efficiency can be achieved. Specifically, when the total weight of the host material content W1, the delayed fluorescent material content W2, and the luminescent material content W3 is assumed to be 100 wt %, the host material content W1 is preferably 15 wt % to 99.9 wt %, 50 wt % to 90 wt %, or 70 wt % to 80 wt %, the delayed fluorescent material content W2 is preferably 5.0 wt % to 50 wt %, 5.0 wt % to 45 wt %, or 10 wt % to 40 wt %, and the luminescent material content W3 is preferably 0.1 wt % to 5.0 wt %, 0.3 wt % to 4.0 wt %, or 0.5 wt % to 3.0 wt %.

(Other Organic Compounds)

The luminescent layer may include the host material, the delayed fluorescent material and the luminescent material only, or may include organic compounds in addition to those. Examples of such organic compounds include organic compounds having carrier (electron and/or hole) transport capability. As the organic compounds having hole transport capability and the organic compounds having electron transport capability, the following hole transport materials and electron transport materials may be referred to, respectively.

[Substrate]

In some example embodiments, it is preferable that the organic EL element of the present invention be supported by a substrate. Any substrate that is conventionally used for organic EL elements may be used without particular limitation, and, for example, a substrate made of glass, transparent plastic, quartz, or silicon may be used.

[Positive Electrode]

A positive electrode of an organic EL element that includes electrode material made of metal, alloy, electrically conductive compound, or mixture thereof having a large work function (4 eV or more) is preferably used. Specific examples of such electrode materials include metals such as Au, and transparent conductive materials such as, CuI, indium tin oxide (ITO), $SnO_2$, and ZnO. Alternatively, amorphous material such as IZO ($In_2O_3$—ZnO) from which a transparent conductive film can be made may be used. In preparation of the positive electrode, a thin film formed from those electrode materials by a method such as deposition or sputtering may be subjected to photolithography to form a pattern with a desired shape, alternatively in the case of not needing a precise pattern (about 100 μm or more), the pattern may be formed through a mask with a desired shape when the electrode material is deposited or sputtered. Alternatively, in the case of using an applicable material such as an organic conductive material, a wet deposition method such as printing and coating may also be used. In the case of producing light from the positive electrode, it is desirable that the transmittance be controlled to be higher than 10%, and it is preferable that the sheet resistance as positive electrode be several hundred Ω/sq. or less. Furthermore, the film thickness is selected usually from a range of 10 to 1000 nm, preferably from a range of 10 to 200 nm, depending on its material.

[Negative Electrode]

A negative electrode that includes electrode material made of metal (referred to as electron injecting metal), alloy, electrically conductive compound, or mixture thereof having a small work function (4 eV or less) is used. Specific examples of such electrode materials include sodium, sodium-potassium alloy, magnesium, lithium, magnesium/copper mixture, magnesium/silver mixture, magnesium/aluminum mixture, magnesium/indium mixture, aluminum/aluminum oxide ($Al_2O_3$) mixture, indium, lithium/aluminum mixture, and rare earth metals. In view of electron injection properties as well as durability against oxidation and the like, a mixture of an electron injecting metal and a stable second metal having a larger work function than the electron injecting metal is preferred, including magnesium/silver mixture, magnesium/aluminum mixture, magnesium/indium mixture, aluminum/aluminum oxide ($Al_2O_3$) mixture, lithium/aluminum mixture, and aluminum. The negative electrode can be manufactured by forming a thin film from these electrode materials by a method such as deposition or sputtering. In some example embodiments, it is preferable that the sheet resistance as negative electrode be several hundred Ω/sq. or less, and the film thickness is selected, usually from a range of 10 nm to 5 μm, preferably from a range of 50 to 200 nm. Also, in order to transmit the emitted light, any one of the positive electrode and the negative electrode of the organic EL element can be transparent or translucent for improvement in luminance. Furthermore, the transparent conductive materials given as examples in the section of positive electrode may be used to manufacture a transparent or translucent negative electrode, and an element with both of the positive electrode and the negative electrode having transparency can be manufactured.

[Injection Layer]

The injection layer is a layer disposed between the electrode and the organic layer for reduction in driving voltage and improvement in luminance, including a hole injection layer and an electron injection layer, which may be present between the positive electrode and the luminescent layer or the hole transport layer, and between the negative electrode and the luminescent layer or the electron transport layer. The injection layer may be disposed on an as needed basis.

[Blocking Layer]

The blocking layer is a layer that can block the diffusion of electric charges (electrons or holes) and/or excitons present in the luminescent layer to the outside of the luminescent layer. The electron blocking layer can be disposed between the luminescent layer and the hole transport layer so as to block the electrons from passing through the luminescent layer toward the hole transport layer. In the same manner, the hole blocking layer can be disposed between the luminescent layer and the electron transport layer so as to block the holes from passing through the luminescent layer toward the electron transport layer. The blocking layer can also be used to block the excitons from diffusing to the outside of the luminescent layer. In other words, each of the electron blocking layer and the hole blocking layer may double as the exciton blocking layer. The electron blocking layer or exciton blocking layer herein means a layer having both functions of the electron blocking layer and the exciton blocking layer in itself.

[Hole Blocking Layer]

The hole blocking layer in a broad sense has the function of an electron transport layer. The hole blocking layer is capable of transporting electrons while blocking holes from reaching the electron transport layer, so that the probability of recombination of electrons and holes in the luminescent layer can be improved.

[Electron Blocking Layer]

The electron blocking layer in a broad sense has the function for transporting holes. The electron blocking layer is capable of transporting holes while blocking electrons from reaching the hole transport layer, so that the probability of recombination of electrons and holes in the luminescent layer can be improved.

[Exciton Blocking Layer]

The exciton blocking layer is a layer for blocking the exciton generated by the recombination of the holes and electrons in the luminescent layer from diffusing into the charge transport layer, which allows the excitons to be efficiently confined in the luminescent layer to thereby improve the luminous efficiency of an element. The exciton blocking layer may be inserted adjacent to the luminescent layer, on any of the positive electrode-side and the negative electrode-side, and insertion on both sides at one time is also possible. In other words, when having the exciton blocking layer on the positive electrode-side, the layer may be inserted between the hole transport layer and the luminescent layer, adjacent to the luminescent layer; and when inserted on the negative electrode-side, the layer may be inserted between the luminescent layer and the negative electrode, adjacent to the luminescent layer. When the exciton blocking layer is inserted adjacent to the luminescent layer on the positive electrode-side, the hole injection layer and the electron blocking layer may be included between the positive electrode and the exciton blocking layer; and when the exciton blocking layer is inserted adjacent to the luminescent layer on the negative electrode-side, the electron injection layer, the electron transport layer, and the hole blocking layer may be included between the negative electrode and the exciton blocking layer. When a blocking layer is disposed, it is preferable that at least any one of the excited singlet energy and the excited triplet energy of the material for use as blocking layer be higher than the excited singlet energy and the excited triplet energy of the luminescent material.

[Hole Transport Layer]

The hole transport layer is made of hole transport material having a function for transporting holes, and can be disposed as a single layer or multiple layers. The hole transport material has any of hole injection or transport properties and electron barrier properties, and may be any of an organic material and an inorganic material. Examples of the hole transport material include a triazole derivative, an oxadiazole derivative, an imidazole derivative, a carbazole derivative, an indolocarbazole derivative, a polyarylalkan derivative, a pyrazoline derivative and a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer, and an electrically conductive polymer/oligomer, particularly a thiophene oligomer. In some example embodiments, it is preferable to use a porphyrin compound, an aromatic tertiary amine compound, and a styrylamine compound, and in still other example embodiments it is more preferable to use an aromatic tertiary amine compound.

[Electron Transport Layer]

The electron transport layer is made of material having a function for transporting electrons, and can be disposed as a single layer or multiple layers. The electron transport material (which doubles as hole blocking material in some cases) functions by transmitting electrons injected from the negative electrode to the luminescent layer. Examples of the electron transport layer include a nitro-substituted fluorene derivative, a diphenylquinone derivative, a thiopyrandioxide derivative, carbodiimide, a fluorenylidene methane derivative, anthraquinodimethane and anthrone derivatives, and an oxadiazole derivative. Furthermore, a thiadiazole derivative obtained by substituting the oxygen atom of the oxadiazole ring of the oxadiazole derivative with a sulfur atom, and a quinoxaline derivative having a quinoxaline ring known as electron-withdrawing group can also be used as the electron transport material. Furthermore, polymer materials having a polymer chain in which these materials are introduced or having a main chain of these materials can also be used.

The deposition method of these layers is not particularly limited, and any of a dry process and a wet process can be employed. For these layers, conventionally known organic compounds such as the compounds described in Patent Literature 1 can be used. Each of the films may include one organic compound only or two or more organic compounds.

The organic EL element having the constituents described above emits light when an electric field is applied between the positive electrode and the negative electrode. According to the organic EL element of the present invention, fluorescence emission due to the excited singlet energy is the main luminescence.

The organic EL element of the present invention can be applied to any of a single element, an element having array structure, and a structure having positive electrode and negative electrode disposed in an X-Y matrix form. The organic EL element of the present invention emits light in a near-infrared range, suitable as, for example, a light source for optical communication, a light source for biometrics, and a light source for sensors, in addition to the bioinstrumentation devices described above.

[Bioinstrumentation Device]

The bioinstrumentation device comprises the organic EL element described above and a photo detector. According to the present device, an organism is exposed to the light in a near-infrared range from the organic EL element as light source for the measurement of the change in the intensity of optical absorption, reflected light, scattered light, and luminescence caused by the biological tissues, so that biological sensing can be performed.

EXAMPLES

Hereinafter, the present invention will be specifically described with reference to Examples, but the present invention is not limited to these Examples. In Examples and Comparative Examples, the relations between abbreviations and formulas are as follows.

[Chemical Formula 18]

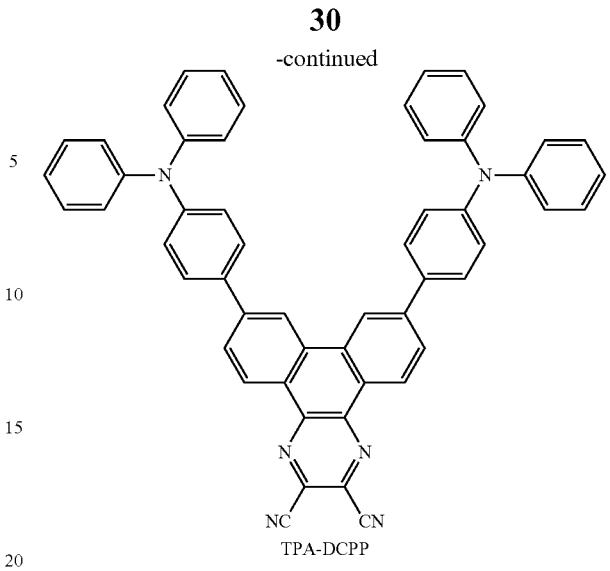

-continued

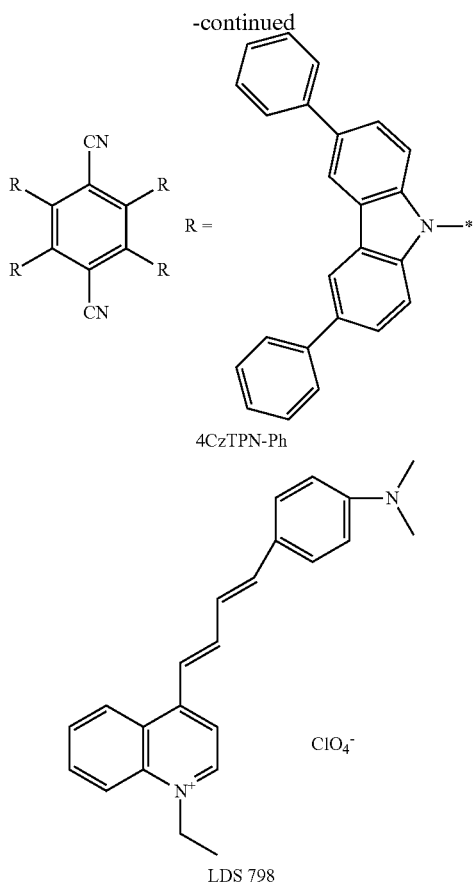

4CzTPN-Ph

LDS 798

<Manufacturing of Organic EL Element>

Example 1

On a glass substrate having a positive electrode made of indium-tin oxide (ITO) with a thickness of 110 nm, an organic layer shown below was laminated by vacuum deposition. First, a layer of HATCN was formed on the ITO, and a layer of TAPC was formed thereon. Subsequently, CBP (host material), TPA-DCPP (delayed fluorescent material), and TPA-ThQ (luminescent material) were co-deposited from different deposition sources, so as to form a luminescent layer. On this occasion, the mass ratio of CBP:TPA-DCPP:TPA-ThQ was set at 75:24:1.0. Subsequently, a layer of T2T was formed, and a layer of BPyTP2 was formed thereon. The total thickness (from HATCN to BPyTP2) of the organic layer formed was 170 nm. Furthermore, lithium fluoride (LiF) was vacuum deposited to a thickness of 0.8 nm, and aluminum (Al) was then deposited to a thickness of 100 nm so as to form a negative electrode, so that the organic EL element was obtained.

Example 2

On a glass substrate having a positive electrode made of indium-tin oxide (ITO) with a thickness of 110 nm, an organic layer shown below was laminated by vacuum deposition. First, a layer of HATCN was formed on the ITO, and a layer of TAPC was formed thereon. Subsequently, CBP (host material), 4CzTPN-Ph (delayed fluorescent material), and TPA-ThQ (luminescent material) were co-deposited from different deposition sources, so as to form a luminescent layer. On this occasion, the mass ratio of CBP:4CzTPN-Ph:TPA-ThQ was set at 75:24:1.0. Subsequently, a layer of T2T was formed, and a layer of BPyTP2 was formed thereon. The total thickness (from HATCN to BPyTP2) of the organic layer formed was 120 nm. Furthermore, lithium fluoride (LiF) was vacuum deposited to a thickness of 0.8 nm, and aluminum (Al) was then deposited to a thickness of 100 nm so as to form a negative electrode, so that the organic EL element was obtained.

Example 3

On a glass substrate having a positive electrode made of indium-tin oxide (ITO) with a thickness of 110 nm, a layer of PEDOT (poly(3,4-ethylene dioxythiophene)):PSS (polystyrene sulfonate) was formed by spin coating and baked at 150° C. Subsequently, CBP (host material), TPA-DCPP (delayed fluorescent material) and TPA-ThQ (luminescent material) were dissolved in chloroform at a concentration of 6 mg/ml in a mass ratio of 75:24:1.0, and the resultant solution was spin-coated on the PEDOT:PSS layer to form a layer, and then baked at 50° C. under nitrogen atmosphere. Subsequently, a layer of T2T was formed by vacuum deposition, and a layer of BPyTP2 was formed thereon. The total thickness (from PEDOT:PSS to BPyTP2) of the formed organic layer was 140 nm. Furthermore, lithium fluoride (LiF) was vacuum deposited to a thickness of 0.8 nm thereon, and aluminum (Al) was then deposited to a thickness of 100 nm so as to form a negative electrode, so that the organic EL element was obtained.

Comparative Example 1

On a glass substrate having a positive electrode made of indium-tin oxide (ITO) with a thickness of 110 nm, a layer of PEDOT:PSS was deposited by spin coating and baked at 150° C. Subsequently, CBP (host material), TPA-DCPP (delayed fluorescent material) and LDS798 (luminescent material) manufactured by Exciton Inc. were dissolved in chloroform at a concentration of 6 mg/ml in a mass ratio of 75:24:1.0, and the resultant solution was spin-coated on the PEDOT:PSS layer to form a layer, and then baked at 50° C. under nitrogen atmosphere. Subsequently, a layer of T2T was formed by vacuum deposition, and a layer of BPyTP2 was formed thereon. The total thickness (from PEDOT:PSS to BPyTP2) of the formed organic layer was 140 nm. Furthermore, lithium fluoride (LiF) was vacuum deposited to a thickness of 0.8 nm thereon, and aluminum (Al) was then deposited to a thickness of 100 nm so as to form a negative electrode, so that the organic EL element was obtained.

<Evaluation>

(Measurement of EL Spectrum)

Figure 2:
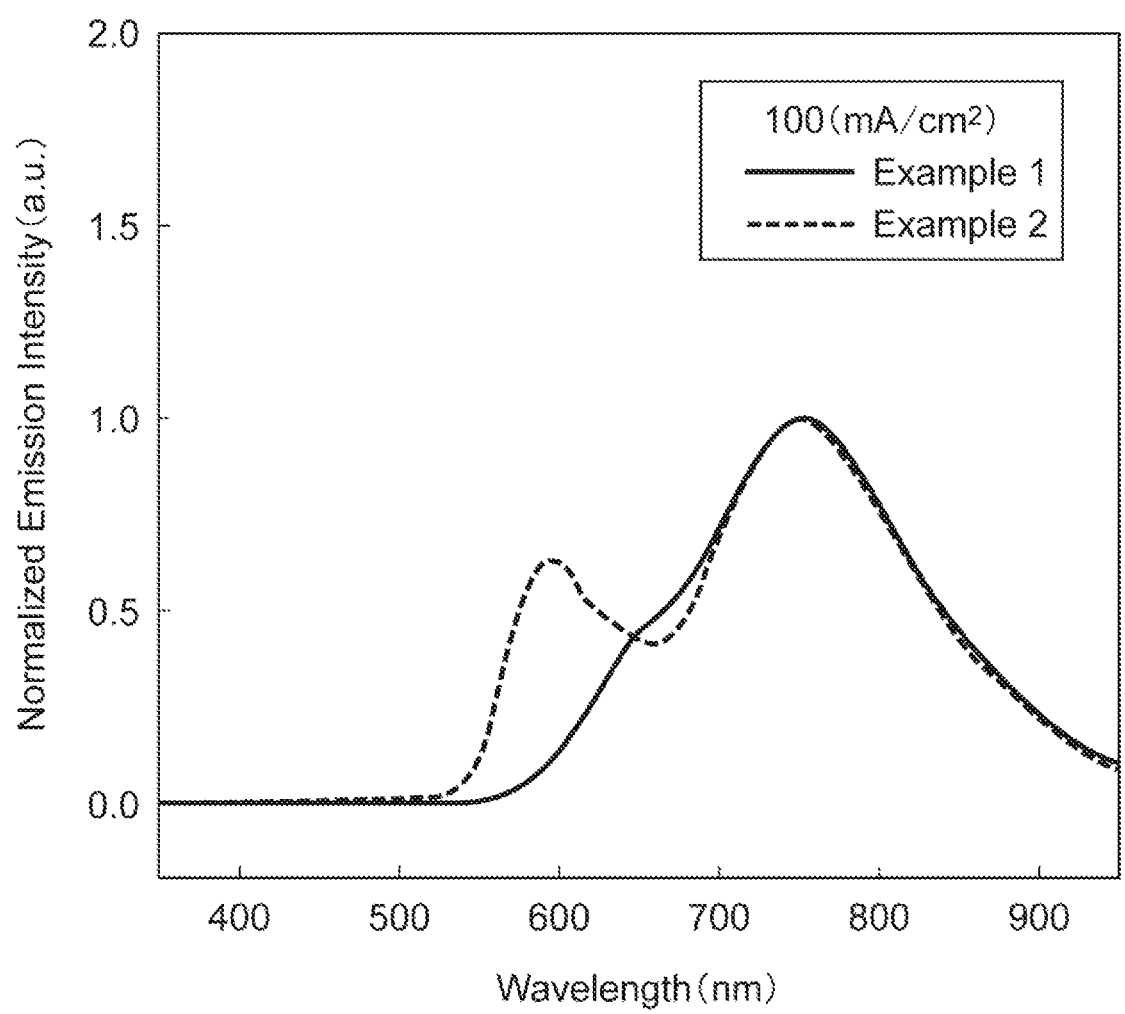
FIG. 2 is a chart showing the EL spectrum of organic EL elements of Examples 1 and 2.
Figure 4:
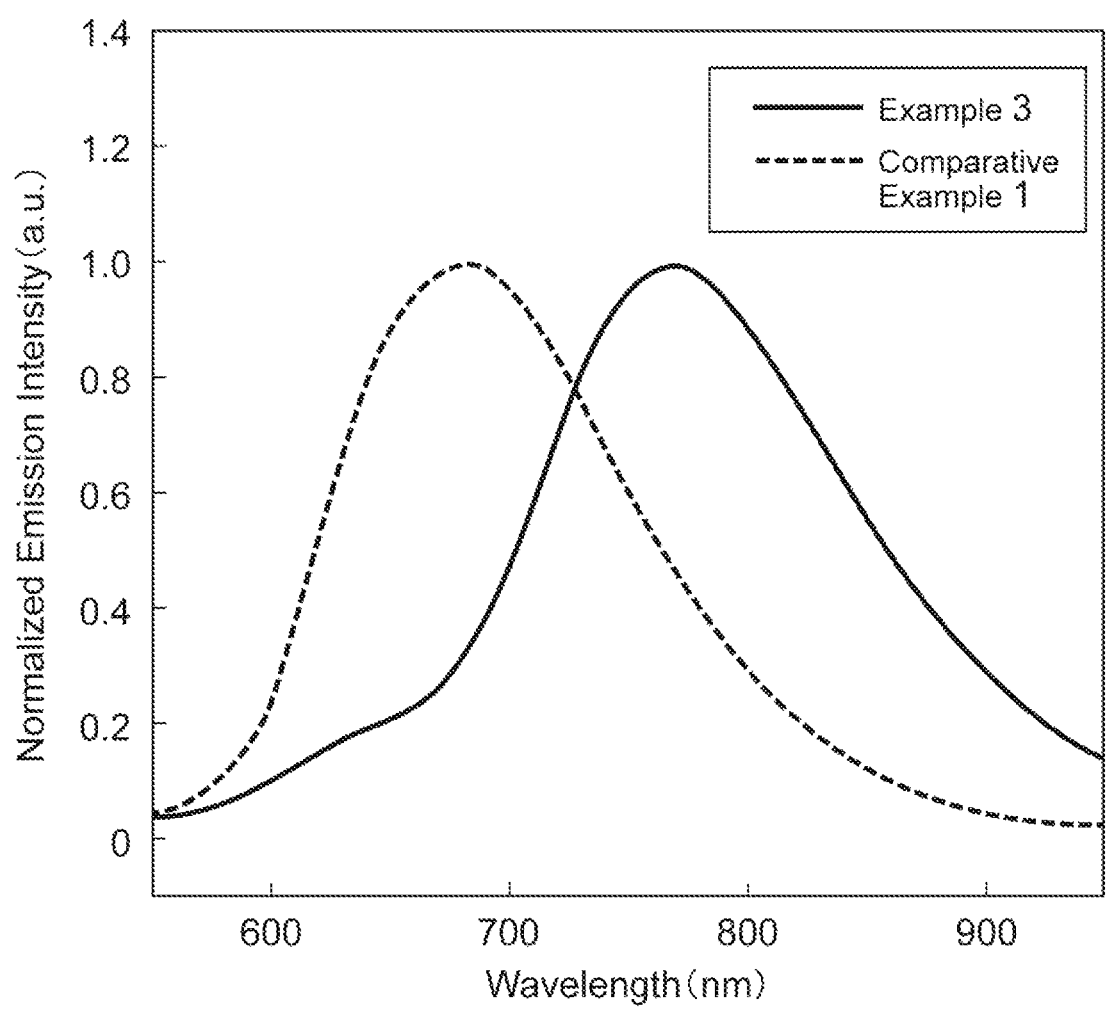
FIG. 4 is a chart showing the EL spectra of organic EL elements of Example 3 and Comparative Example 1.

The organic EL elements obtained in Examples and Comparative Example were subjected to the measurement of EL spectrum. The results are shown in FIG. 2 and FIG. 4. As shown in FIG. 2, the organic EL elements of Examples 1 and 2 have the maximum luminescence in a near-infrared range of 700 nm or more (near a wavelength of 760 nm). As shown in FIG. 4, while the organic EL element of Example 3 has the maximum luminescence in the near-infrared range (near a wavelength of 770 nm), the organic EL element of Comparative Example 1 has the maximum luminescence outside the near-infrared range (near a wavelength of 680 nm).

(Measurement of External Quantum Efficiency (EQE))

Figure 3:
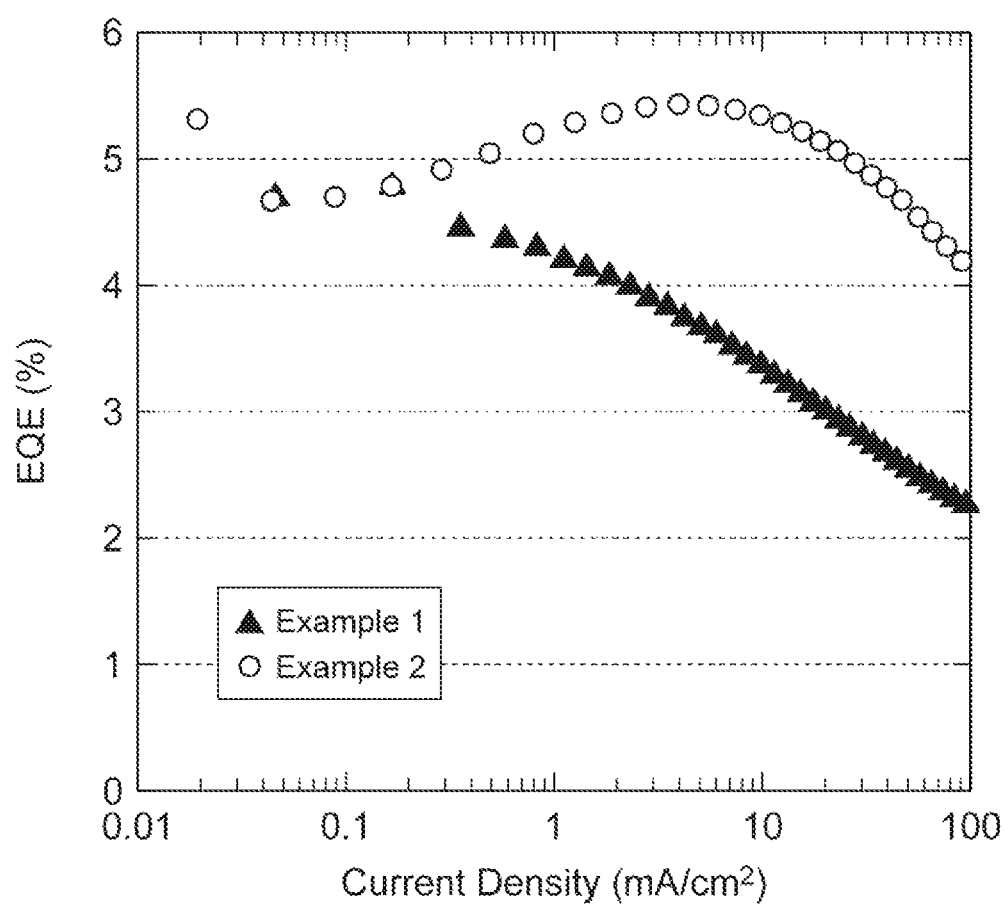
FIG. 3 is a chart showing the external quantum efficiency (EQE) of organic EL elements of Examples 1 and 2.
Figure 5:
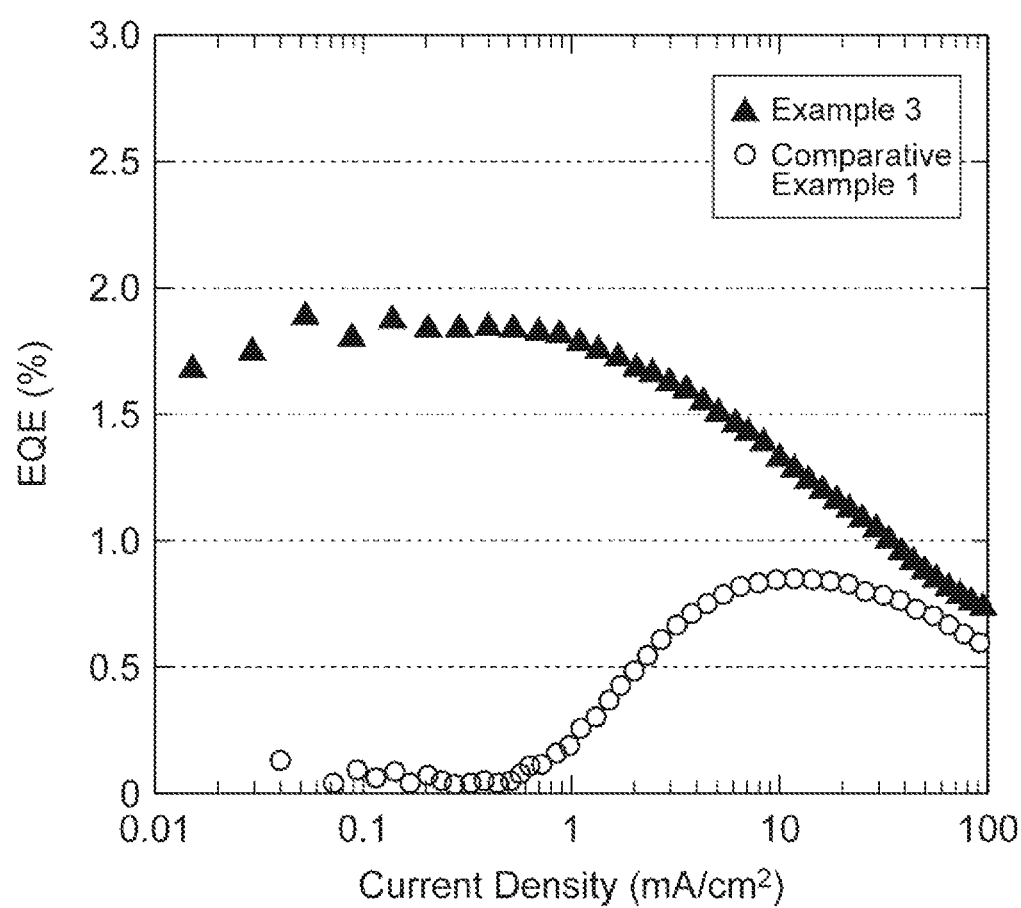
FIG. 5 is a chart showing the external quantum efficiency (EQE) of organic EL elements of Example 3 and Comparative Example 1.

The organic EL elements having a luminescent area of 4 mm² obtained in Examples and Comparative Example were encapsulated under nitrogen atmosphere, and then subjected to the measurement of external quantum efficiency (EQE) under the air atmosphere using an external quantum efficiency measurement device C9920-12 (manufactured by Hamamatsu Photonics K.K.). As preparation before the measurement, absorption correction was performed using a halogen light source L6758-21 (manufactured by Hamamatsu Photonics K.K.) and the manufactured organic EL elements. Under measurement conditions with an exposure time based on auto gain, and an averaging of 2 times or more, the EQE value at the current value corresponding to an intensity (number of counts) of the luminescence peak value of 0.2 or more was employed. The results are shown in FIG. 3 and FIG. 5.

As clear from the foregoing results, organic EL elements of Examples 1 to 3 have the maximum luminescence in a near-infrared range with a relatively high luminous efficiency, while the organic EL element of Comparative Example 1 has the maximum luminescence outside the near-infrared range with a relatively low luminous efficiency. Hereinafter, Example 3 and Comparative Example 1, in which the organic EL elements were made under the same conditions except that different luminescent materials were used, are examined in more detail.

TPA-DCPP as the delayed fluorescent material in Example 3 and Comparative Example 1 is a material having a luminescence peak at a wavelength near 650 nm, while TPA-ThQ and LDS798 as the luminescent materials in Example 3 and Comparative Example 1 are materials having luminescence peaks at a wavelength near 770 nm and at a wavelength near 700 nm, respectively, without the presence of the delayed fluorescent material. When the energy transfer from the delayed fluorescent material to the luminescent material occurs with high efficiency, the ratio of the emission intensity of the luminescent material to the emission intensity of the delayed fluorescent material increases, so that the luminescence of the organic EL element as a whole comes near the luminescence peak of the luminescent material without delayed fluorescent material. From this viewpoint, the luminescence peak of the organic EL element of Example 3 is at almost the same wavelength as the luminescent material without delayed fluorescent material (near a wavelength of 770 nm), and it can thus be found that the energy transfer from the delayed fluorescent material to the luminescent material occurs with high efficiency. On the other hand, the luminescence peak of the organic EL element of Comparative Example 1 (near a wavelength of 680 nm) is smaller than when using the luminescent material without delayed fluorescent material (near a wavelength of 700 nm), and it can thus be found that the efficiency of energy transfer from the delayed fluorescent material to the luminescent material is relatively low. Furthermore, the external quantum efficiency of the organic EL element of Example 3 is superior to the external quantum efficiency of the organic EL element of Comparative Example 1.

It is to be understood that not all aspects, advantages and features described herein may necessarily be achieved by, or included in, any one particular example embodiment. Indeed, having described and illustrated various examples herein, it should be apparent that other examples may be modified in arrangement and detail. We claim all modifications and variations coming within the spirit and scope of the subject matter claimed herein.

The invention claimed is:

1. An organic electro-luminescent element having a luminescence peak in a near-infrared range, comprising a positive electrode, a negative electrode, and at least one organic layer including a luminescent layer located between the positive electrode and the negative electrode, wherein the luminescent layer comprises:

a host material;

a delayed fluorescent material as an assistant dopant; and a luminescent material as a dopant, wherein each of the delayed fluorescent material and the luminescent material has a N-containing structure with two or three benzene rings bonded to an N atom, wherein the N-containing structure of each of the delayed fluorescent material and the luminescent material comprises a structure selected from formulas (1) to (6):

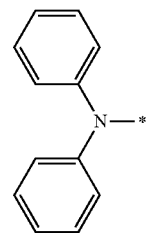

(1)

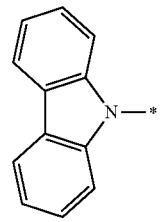

(2)

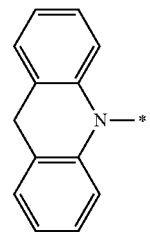

(3)

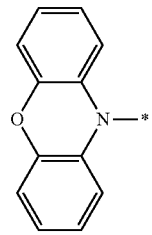

(4)

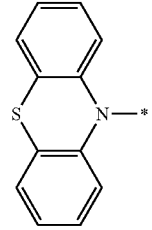

(5)

-continued

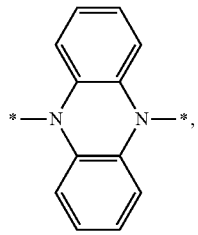
(6)

the structure of the delayed fluorescent material selected from formulas (1) to (6) is also selected as the N-containing structure of the luminescent material, and
each of the delayed fluorescent material and the luminescent material further has a fused ring structure in addition to the N-containing structure, wherein the fused ring structures of the delayed fluorescent material and the luminescent material each comprise an equivalent set of at least two successive rings selected from the following group:

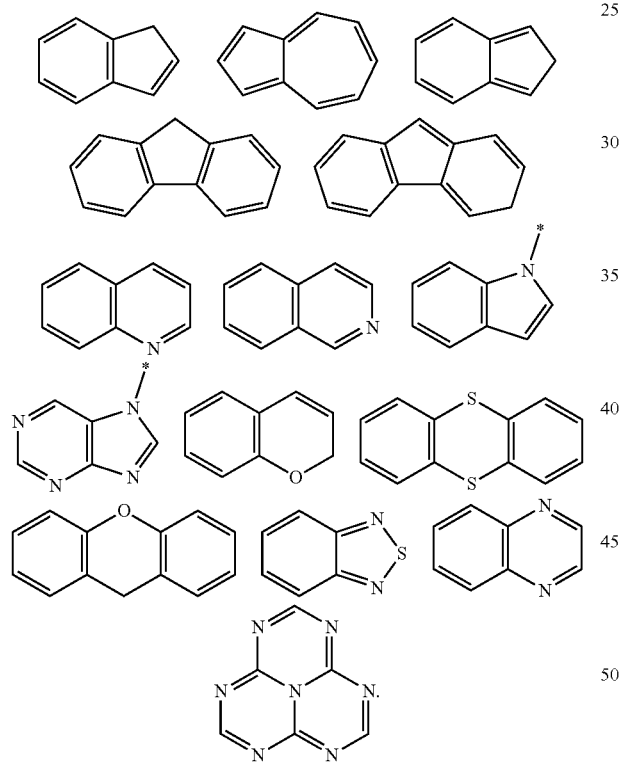

2. An organic electro-luminescent element having a luminescence peak in a near-infrared range, comprising a positive electrode, a negative electrode, and at least one organic layer including a luminescent layer located between the positive electrode and the negative electrode, wherein the luminescent layer comprises:
   a host material;
   a delayed fluorescent material as an assistant dopant; and
   a luminescent material as a dopant, wherein each of the delayed fluorescent material and the luminescent material has a N-containing structure with two or three benzene rings bonded to an N atom, wherein the N-containing structure of each of the delayed fluorescent material and the luminescent material is selected from formulas (1) to (6):

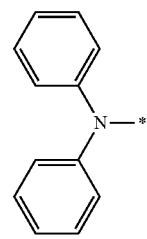
(1)

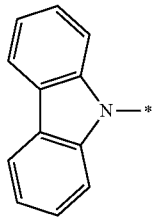
(2)

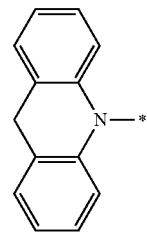
(3)

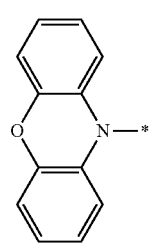
(4)

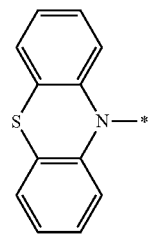
(5)

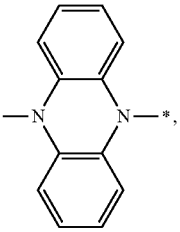
(6)

and
each of the delayed fluorescent material and the luminescent material further has a fused ring structure in addition to the N-containing structure, wherein the fused ring structures of the delayed fluorescent material and the luminescent material each having an equivalent set of at least two successive rings selected from the following group:

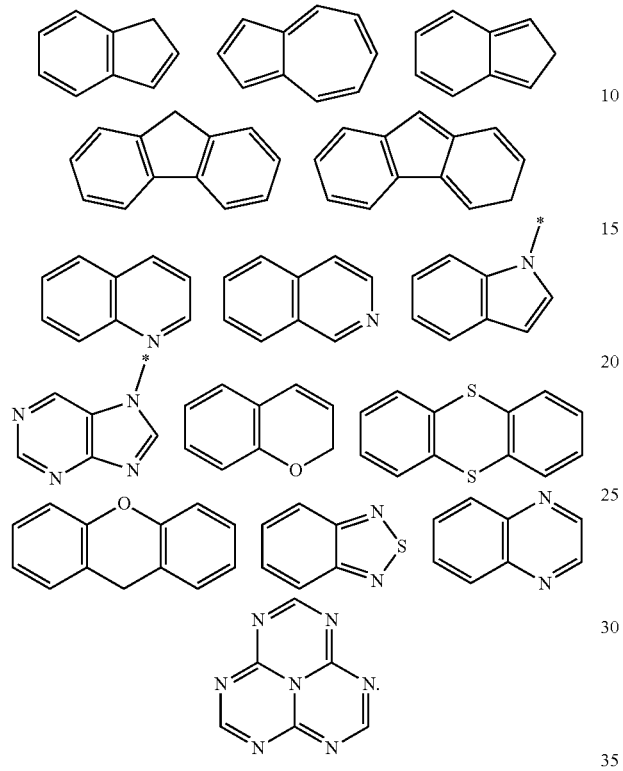

3. The organic electro-luminescent element according to claim 1, wherein the N-containing structure comprises a structure represented by formula (7):

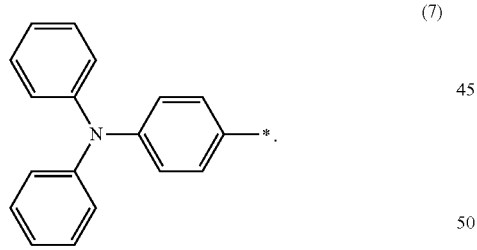

(7)

4. A bioinstrumentation device comprising:
a photo detector; and
an organic electro-luminescent element having a luminescence peak in a near-infrared range, comprising a positive electrode, a negative electrode, and at least one organic layer including a luminescent layer located between the positive electrode and the negative electrode, wherein the luminescent layer comprises:
a host material;
a delayed fluorescent material as an assistant dopant; and
a luminescent material as a dopant, wherein each of the delayed fluorescent material and the luminescent material has a N-containing structure with two or three benzene rings bonded to an N atom, wherein the N-containing structure of each of the delayed fluorescent material and the luminescent material is selected from formulas (1) to (6):

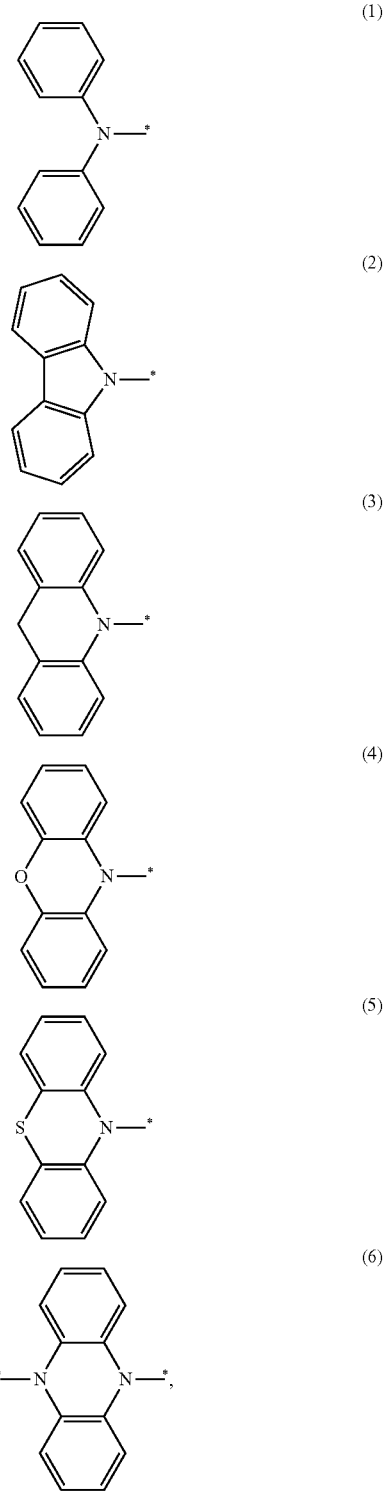

and
each of the delayed fluorescent material and the luminescent material further has a fused ring structure in addition to the N-containing structure, wherein the fused ring structures of the delayed fluorescent material and the luminescent material each having an equivalent set of at least two successive rings selected from the following group:

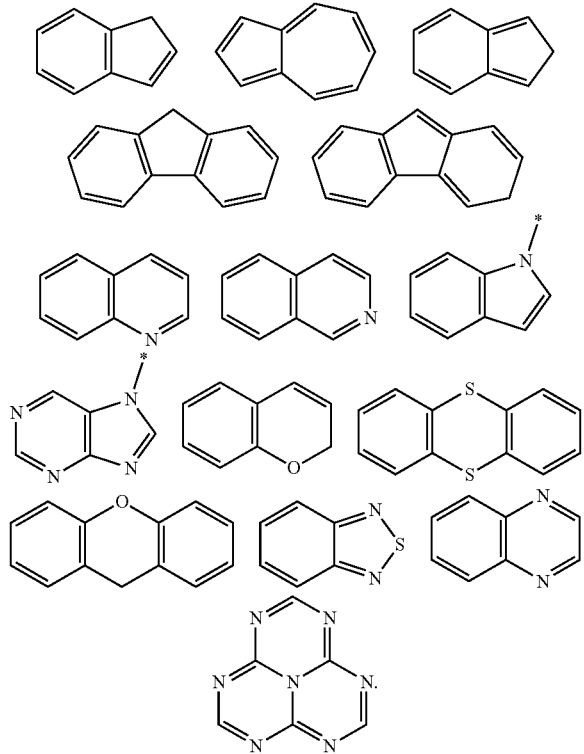

5. The bioinstrumentation device according to claim 4, wherein the structure of the delayed fluorescent material selected from formulas (1) to (6) is the same as the N-containing structure of the luminescent material.

6. The bioinstrumentation device according to claim 4, wherein the N-containing structure of at least one of the delayed fluorescent material and the luminescent material comprises a structure represented by formula (7):

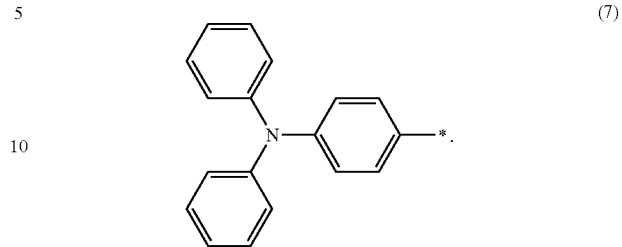

(7)

7. The bioinstrumentation device according to claim 6, wherein each of the delayed fluorescent material and the luminescent material has the N-containing structure represented by formula (7).

8. The organic electro-luminescent element according to claim 1, wherein a content of the host material is 50 wt % to 90 wt %, a content of the delayed fluorescent material is 5.0 wt % to 45 wt %, and a content of the luminescent material is 0.3 wt % to 4.0 wt % based on a total content of the host material, the delayed fluorescent material, and the luminescent material.

9. The organic electro-luminescent element according to claim 2, wherein a content of the host material is 50 wt % to 90 wt %, a content of the delayed fluorescent material is 5.0 wt % to 45 wt %, a content of the luminescent material is 0.3 wt % to 4.0 wt % based on a total content of the host material, the delayed fluorescent material, and the luminescent material.

10. The bioinstrumentation device according to claim 4, wherein a content of the host material is 50 wt % to 90 wt %, a content of the delayed fluorescent material is 5.0 wt % to 45 wt %, a content of the luminescent material is 0.3 wt % to 4.0 wt % based on a total content of the host material, the delayed fluorescent material, and the luminescent material.

* * * * *